United States Patent
Akiyama

(10) Patent No.: US 12,076,277 B2
(45) Date of Patent: Sep. 3, 2024

(54) PHOTOCOAGULATION APPARATUS, CONTROL METHOD OF PHOTOCOAGULATION APPARATUS, AND RECORDING MEDIUM

(71) Applicant: Topcon Corporation, Tokyo (JP)

(72) Inventor: Hiroshi Akiyama, Souka (JP)

(73) Assignee: TOPCON CORPORATION, Tokyo (JP)

( * ) Notice: Subject to any disclaimer, the term of this patent is extended or adjusted under 35 U.S.C. 154(b) by 911 days.

(21) Appl. No.: 17/258,744

(22) PCT Filed: Jun. 6, 2019

(86) PCT No.: PCT/JP2019/022575
§ 371 (c)(1),
(2) Date: Jan. 8, 2021

(87) PCT Pub. No.: WO2020/012841
PCT Pub. Date: Jan. 16, 2020

(65) Prior Publication Data
US 2021/0267801 A1    Sep. 2, 2021

(30) Foreign Application Priority Data

Jul. 11, 2018   (JP) ................. 2018-131249

(51) Int. Cl.
*A61F 9/008* (2006.01)
*G06T 11/00* (2006.01)
(Continued)

(52) U.S. Cl.
CPC ...... *A61F 9/00823* (2013.01); *A61F 9/00821* (2013.01); *G06T 11/008* (2013.01);
(Continued)

(58) Field of Classification Search
None
See application file for complete search history.

(56) References Cited

U.S. PATENT DOCUMENTS

| RE46,493 E | 8/2017 | Lin |
| 2004/0039378 A1 | 2/2004 | Lin |

(Continued)

FOREIGN PATENT DOCUMENTS

| EP | 3533384 A1 | 9/2019 | |
| EP | 3533384 B1 * | 9/2021 | ............... A61B 3/10 |

(Continued)

OTHER PUBLICATIONS

English Translation JP2016159068A.*

(Continued)

*Primary Examiner* — Allen Porter
*Assistant Examiner* — James Moss
(74) *Attorney, Agent, or Firm* — XSENSUS LLP

(57) ABSTRACT

A photocoagulation apparatus of some embodiment examples is configured to apply both treatment light for subthreshold coagulation and an OCT scan to a retina via a probe inserted in an eye. Upon receiving a user's instruction, the apparatus applies the treatment light to the retina, and applies an OCT scan to the retina at least after the treatment light application. The apparatus compares the first OCT image constructed from OCT data of the retina acquired prior to the treatment light application and the second OCT image constructed from OCT data of the retina acquired after the treatment light application, thereby acquiring change information that represents a tissue change in the retina caused by the treatment light. The apparatus displays a change image based on the change information together with a retinal image.

15 Claims, 19 Drawing Sheets

(51) Int. Cl.
*G16H 15/00* (2018.01)
*G16H 20/40* (2018.01)
*G16H 30/20* (2018.01)
*G16H 30/40* (2018.01)
*G16H 40/60* (2018.01)
*G16H 50/50* (2018.01)
*G16H 50/70* (2018.01)
*A61B 18/20* (2006.01)
*A61B 90/00* (2016.01)

(52) U.S. Cl.
CPC ............. *G16H 15/00* (2018.01); *G16H 20/40* (2018.01); *G16H 30/20* (2018.01); *G16H 30/40* (2018.01); *G16H 40/60* (2018.01); *G16H 50/50* (2018.01); *G16H 50/70* (2018.01); *A61B 2018/2005* (2013.01); *A61B 2090/3735* (2016.02); *A61F 2009/00851* (2013.01); *A61F 2009/00863* (2013.01); *G06T 2211/428* (2013.01)

(56) References Cited

U.S. PATENT DOCUMENTS

| | | |
|---|---|---|
| 2006/0161145 A1 | 7/2006 | Lin et al. |
| 2006/0259022 A1 | 11/2006 | Lin |
| 2008/0259422 A1 | 10/2008 | Lin |
| 2008/0281306 A1 | 11/2008 | Lin |
| 2008/0300581 A1 | 12/2008 | Wiechmann et al. |
| 2010/0057059 A1* | 3/2010 | Makino ............ A61B 3/113 606/4 |
| 2010/0228238 A1* | 9/2010 | Brennan ............ A61B 5/0073 600/476 |
| 2012/0296320 A1 | 11/2012 | Lin et al. |
| 2014/0288537 A1 | 9/2014 | Wiechmann et al. |
| 2014/0324031 A1 | 10/2014 | Abe |
| 2015/0168127 A1 | 6/2015 | Takeno et al. |
| 2015/0374228 A1 | 12/2015 | Satake et al. |
| 2016/0256324 A1 | 9/2016 | Suzuki |
| 2016/0278983 A1* | 9/2016 | Claus ............ A61F 9/00821 |
| 2017/0100285 A1* | 4/2017 | Hallen ............ A61B 5/14555 |
| 2017/0252213 A1* | 9/2017 | Furuuchi ............ A61F 9/00821 |
| 2017/0280989 A1* | 10/2017 | Heeren ............ A61B 1/01 |
| 2018/0172426 A1 | 6/2018 | Takeno et al. |
| 2018/0360655 A1* | 12/2018 | Berlin ............ A61B 3/145 |

FOREIGN PATENT DOCUMENTS

| | | | |
|---|---|---|---|
| JP | 2009-513279 A | | 4/2009 |
| JP | 2009-516552 A | | 4/2009 |
| JP | 2014-230743 A | | 12/2014 |
| JP | 2015-131107 A | | 7/2015 |
| JP | 2016-10656 A | | 1/2016 |
| JP | 2016-159068 A | | 9/2016 |
| JP | 2016-159070 A | | 9/2016 |
| JP | 2016159068 A | * | 9/2016 |
| JP | 2016-194459 A | | 11/2016 |
| JP | 2016-206348 A | | 12/2016 |
| JP | 2017-12431 A | | 1/2017 |
| JP | 2017-153751 A | | 9/2017 |
| JP | 2017-209385 A | | 11/2017 |
| JP | 2018-68545 A | | 5/2018 |
| JP | 2018-86272 A | | 6/2018 |

OTHER PUBLICATIONS

Japanese Office Action issued Jun. 28, 2022, in Japanese Application No. 2018-131249.

International Search Report and Written Opinion mailed on Jul. 23, 2019, received for PCT Application PCT/JP2019/022575, Filed on Jun. 6, 2019, 9 pages including English Translation.

* cited by examiner

PHOTOCOAGULATION APPARATUS, CONTROL METHOD OF PHOTOCOAGULATION APPARATUS, AND RECORDING MEDIUM

CROSS-REFERENCE TO RELATED APPLICATIONS

This application is a national stage (under 35 U.S.C. 371) of International Patent Application No. PCT/JP2019/022575, filed Jun. 6, 2019, claiming priority to Japanese Patent Application No. 2018-131249, filed Jul. 11, 2018, both of which are herein incorporated by reference in their entirety.

FIELD

The present disclosure relates to a photocoagulation apparatus, a method of controlling a photocoagulation apparatus, and a recording medium.

BACKGROUND

Photocoagulation is widely used in ophthalmic treatment. Photocoagulation is a treatment method or technique in which retinal tissue is coagulated by the heat generated by the absorption of laser light energy into the retinal pigment epithelium.

Photocoagulation is used for the following purposes, for example: for thermally destroying and adhering tissues in order to reinstate a detached retina to the retinal pigment epithelium: for thermally destroying an area around a retinal tear (break, hole) to prevent the retinal detachment from spreading so that the retinal tear does not deteriorate; and for burning (and sealing off) new blood vessels to stop or prevent bleeding of the eye fundus. In these applications, a target tissue is sufficiently cauterized and destroyed.

On the other hand, there is also a photocoagulation treatment method or technique that minimizes tissue cauterization. Such treatments are called subthreshold coagulation, micropulse subthreshold coagulation, selective pigment epithelial coagulation, or the like. Hereinafter, such a method or technique will be referred to as "subthreshold coagulation". Subthreshold coagulation is used, for example, for the following purposes: for destroying or damaging photoreceptor cells to reduce retinal metabolism in order to prevent the development of new blood vessels; and for destroying or damaging photoreceptor cells to reduce retinal metabolism in order to reduce diabetic macular edema.

Conventionally, photocoagulation has been performed while checking the degree of cauterization by observing a coagulation spot that appears on the surface of the retina. This conventional method or technique can be effective in photocoagulation for the purpose of sufficient cauterization of a tissue in which a cauterized area extends to the retinal surface. However, the conventional method or technique cannot be employed in subthreshold coagulation because no coagulation spot appears on the retinal surface in subthreshold coagulation.

Note that some techniques or technologies have also been developed to detect a tissue change that does not appear on the retinal surface (i.e., a tissue change in a deep part of the retina) using optical coherence tomography (OCT). However, it is still difficult to create a visualization of the state of a tissue change attributable to subthreshold coagulation in real time and to present the visualization to the user. In particular, it is extremely difficult to properly conduct subthreshold coagulation via a probe inserted into an eye.

BRIEF SUMMARY

An object of the present disclosure is to properly perform a visualization of a tissue change in a deep part of a retina that occurs in subthreshold coagulation.

The first aspect of some embodiment examples is a photocoagulation apparatus for applying subthreshold coagulation to a retina via a probe inserted in an eye, comprising: a laser projecting system configured to apply treatment light for subthreshold coagulation to the retina via the probe: a first optical coherence tomography (OCT) system configured to apply an OCT scan to the retina via the probe: a controller configured to perform, upon receiving an instruction from a user, control of the laser projecting system to apply the treatment light to the retina and control of the first OCT system to apply an OCT scan to the retina at least after application of the treatment light: a first memory that stores a first OCT image constructed from data acquired by an OCT scan applied to the retina prior to the application of the treatment light: an image constructing processor configured to construct a second OCT image from data acquired by the OCT scan applied to the retina after the application of the treatment light: a change information acquiring processor configured to acquire change information representing a tissue change in the retina caused by the treatment light by comparing the first OCT image and the second OCT image with each other; and a display controller configured to display a change image based on the change information on a display device together with a retinal image.

The second aspect of some embodiment examples is the photocoagulation apparatus of the first aspect, wherein the controller performs first control of the first OCT system to apply an OCT scan to the retina to acquire the first OCT image, performs control of the laser projecting system to apply the treatment light to the retina after the first control, and performs second control of the first OCT system to apply an OCT scan to acquire the second OCT image after the control of the laser projecting system.

The third aspect of some embodiment examples is the photocoagulation apparatus of the second aspect, wherein each of the OCT scan applied by the first control and the OCT scan applied by the second control is an A-scan.

The fourth aspect of some embodiment examples is the photocoagulation apparatus of the first aspect, wherein the first OCT image is a three dimensional OCT image constructed from data acquired by applying an OCT scan to a three dimensional region of the retina.

The fifth aspect of some embodiment examples is the photocoagulation apparatus of the fourth aspect, wherein the OCT scan applied to the retina after the application of the treatment light is an A-scan.

The sixth aspect of some embodiment examples is the photocoagulation apparatus of any of the first to fifth aspects, wherein the controller performs the control of the first OCT system to apply the OCT scan to the retina each time the control of the laser projecting system to apply the treatment light to the retina is performed, the image constructing processor constructs the second OCT image each time the OCT scan is applied by the first OCT system, the change information acquiring processor acquires the change information each time the second OCT image is constructed by the image constructing processor, and the display controller updates a display of a change image provided to the user together with the retinal image each time the change information is acquired by the change information acquiring processor.

The seventh aspect of some embodiment examples is the photocoagulation apparatus of the sixth aspect, wherein the controller performs the control of the first OCT system to apply the OCT scan to the retina immediately after the control of the laser projecting system to apply the treatment light to the retina.

The eighth aspect of some embodiment examples is the photocoagulation apparatus of any of the first to seventh aspects, further comprising a second OCT system configured to apply an OCT scan, after the treatment light is applied to each of a plurality of positions on the retina, to an area that includes all of the plurality of positions, wherein the image constructing processor constructs a third OCT image from data acquired by the second OCT system, the change information acquiring processor acquires first change distribution information representing a distribution of tissue changes in the retina in the area by comparing the first OCT image and the third OCT image with each other, and the display controller controls the display device to display a first change distribution image based on the first change distribution information together with a retinal image.

The ninth aspect of some embodiment examples is the photocoagulation apparatus of the eighth aspect, wherein the change information acquiring processor acquires second change distribution information representing a distribution of tissue changes in the retina in the area that includes all of the plurality of positions by comparing the second OCT image and the third OCT image with each other, and the display controller controls the display device to display a second change distribution image based on the second change distribution information together with a retinal image.

The tenth aspect of some embodiment examples is the photocoagulation apparatus of any of the first to ninth aspects, wherein the change information acquiring processor constructs motion contrast data from two or more OCT images acquired from substantially a same position of the retina at different times, and determines a tissue change in the retina from the motion contrast data.

The eleventh aspect of some embodiment examples is the photocoagulation apparatus of any of the first to tenth aspects, wherein the display controller displays the retinal image on a first layer, and displays, on a second layer overlaid on the first layer, an image based on information acquired by the change information acquiring processor.

The twelfth aspect of some embodiment examples is the photocoagulation apparatus of the eleventh aspect, wherein the display controller displays an application condition of the treatment light applied to the retina by the laser projecting system together with the image based on the information acquired by the change information acquiring processor.

The thirteenth aspect of some embodiment examples is the photocoagulation apparatus of any of claims 1 to 12, further comprising: a second memory that stores a template of a treatment report in advance; and a report creating processor configured to enter data in the template based at least on information acquired by the change information acquiring processor.

The fourteenth aspect of some embodiment examples is the photocoagulation apparatus of any of the first to thirteenth aspects, wherein the retinal image is any of an image of the retina acquired by a fundus camera, an image of the retina acquired by a scanning laser ophthalmoscope, an image of the retina acquired by a surgical microscope, an image of the retina acquired by a slit lamp microscope, and a front image of the retina acquired by using OCT.

The fifteenth aspect of some embodiment examples is the photocoagulation apparatus of any of claims 1 to 13, further comprising: an observation system configured for the user to observe a magnified image of the retina via an eyepiece; and an optical path coupling member configured to couple an optical path starting from the display device with an optical path of the observation system toward the eyepiece.

The sixteenth aspect of some embodiment examples is a method of controlling a photocoagulation apparatus that includes a laser projecting system configured to apply treatment light for subthreshold coagulation to a retina via a probe inserted in an eye and an optical coherence tomography (OCT) system configured to apply an OCT scan to the retina via the probe, the method comprising: a control step of performing, upon receiving an instruction from a user, control of the laser projecting system to apply the treatment light to the retina and control of the OCT system to apply an OCT scan to the retina at least after the application of the treatment light: a memory step of storing a first OCT image constructed from data acquired by an OCT scan applied to the retina prior to the application of the treatment light: an image constructing step of constructing a second OCT image from data acquired by the OCT scan applied to the retina after application of the treatment light: a change information acquiring step of acquiring change information representing a tissue change in the retina caused by the treatment light by comparing the first OCT image and the second OCT image with each other; and a display control step of displaying a change image based on the change information on a display device together with a retinal image.

The seventeenth aspect of some embodiment examples is a program configured to cause a computer to execute the method of the sixteenth aspect.

The eighteenth aspect of some embodiment examples is a computer-readable non-transitory recording medium that stores the program of the seventeenth aspect.

According to the embodiment example, a proper visualization of a tissue change in a deep part of a retina that occurs in subthreshold coagulation can be achieved.

DRAWINGS

DETAILED DESCRIPTION

Figure 1:
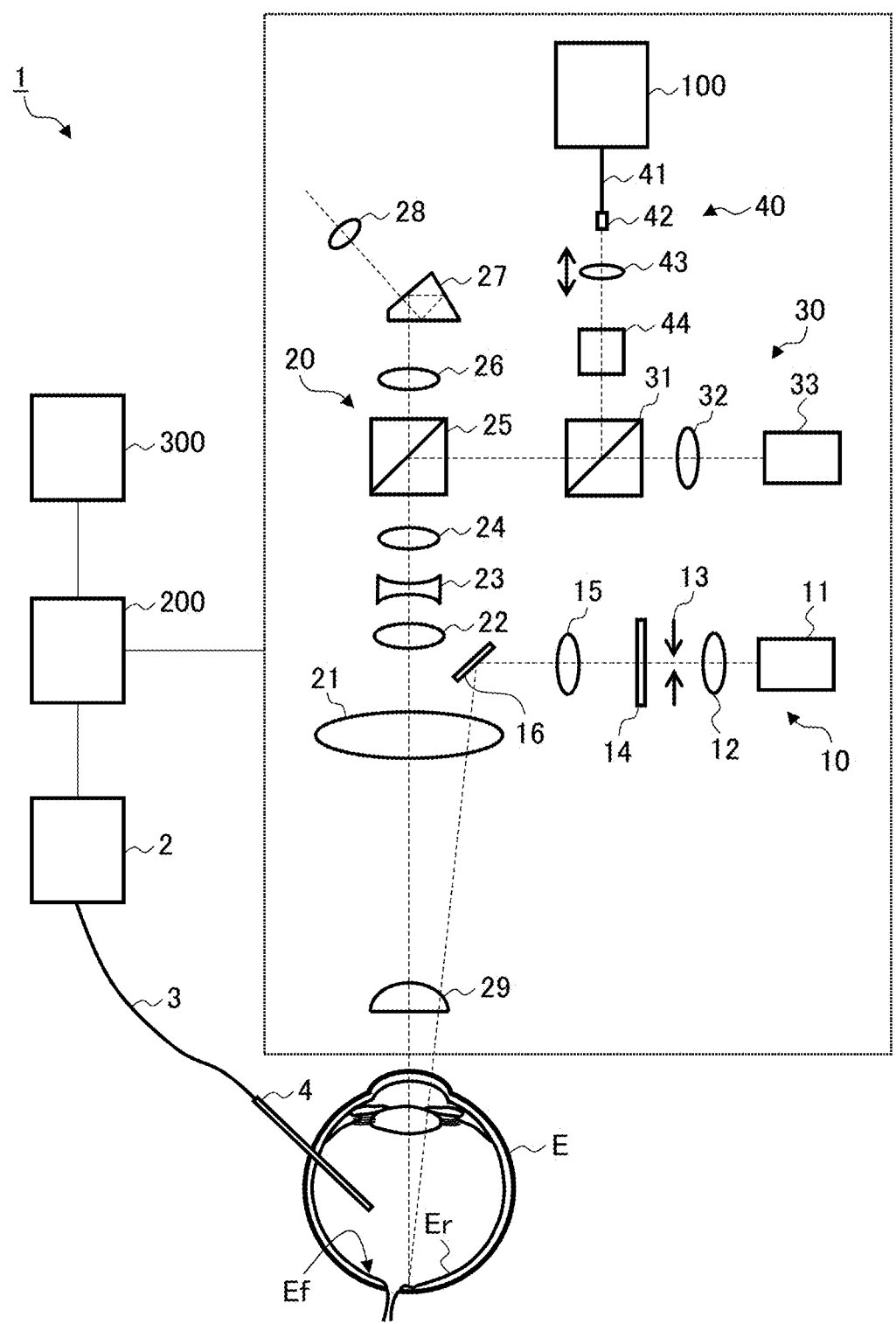
FIG. 1 is a schematic diagram illustrating the configuration of the photocoagulation apparatus according to the embodiment example.

The present disclosure provides descriptions of some embodiment examples of a photocoagulation apparatus, a method of controlling a photocoagulation apparatus, a program, and a recording medium with referring to the drawings. Any known techniques or technologies, including the items and matters disclosed in the documents cited herein, may be combined with the embodiment examples.

In the following disclosure, swept source OCT is employed as a method of optical coherence tomography (OCT). The method of OCT applicable to embodiment examples is not limited to swept source OCT, and may be spectral domain OCT, for example.

Swept source OCT is an imaging technique to construct an image performed by: splitting light emitted from a wavelength tunable light source into measurement light and reference light: superposing return light of the measurement light returning from the object with the reference light to generate interference light: detecting the interference light by a photodetector such as a balanced photodiode; and applying Fourier transform and other processes to the detection data acquired according to the wavelength sweeping and the measurement light scanning.

Spectral domain OCT is an imaging technique to construct an image performed by: splitting light from a low coherence light source into measurement light and reference light; superposing return light of the measurement light returning from the object with the reference light to generate interference light: detecting the spectral distribution of the interference light using a spectrometer; and applying Fourier transform and other processes to the spectral distribution detected.

As described above, swept source OCT is an OCT technique for acquiring a spectral distribution by time division, and spectral domain OCT is an OCT technique for acquiring a spectral distribution by space division. In addition, OCT techniques applicable to embodiment examples are not limited to these two, and may be any other morphological (structural) imaging OCT techniques such as time domain OCT or any functional imaging OCT techniques such as polarization OCT or blood flow measurement OCT.

In the present disclosure, "image data" and an "image" displayed based thereon may not be distinguished from one another unless otherwise mentioned. Likewise, a site or a tissue of the patient's eye and an image representing the site or the tissue may not be distinguished from one another unless otherwise mentioned.

<Configuration of Photocoagulation Apparatus>

FIG. 1 shows the configuration of the photocoagulation apparatus according to the present embodiment example. In general, the photocoagulation apparatus includes a configuration for applying laser light for photocoagulation (subthreshold coagulation) to the retina, and a configuration for observing a magnified image of the eye fundus.

The configuration for applying laser light to the retina may be the same as conventional configurations. For example, the configuration disclosed in Japanese Unexamined Patent Application Publication No. 2016-159070 or any modification thereof may be applied to the present embodiment example.

In the present embodiment example, a microscope for ophthalmic surgery is employed for magnified observation of the eye fundus. As an example of such a microscope for ophthalmic surgery, the one disclosed in Japanese Unexamined Patent Application Publication No. 2016-206348 is known. On the other hand, an ophthalmic microscope of any type such as a slit lamp microscope may be used for magnified observation of the eye fundus.

The photocoagulation apparatus 1 shown in FIG. 1 includes the optical unit 2, the illumination system 10, the observation system 20, the photography system 30, the OCT system 40, and the computer 200. The display device 300 may be included in the photocoagulation apparatus 1 or may be a peripheral device connected to the photocoagulation apparatus 1 (the computer 200).

<Optical Unit 2>

The optical unit 2 includes various kinds of optical elements. The optical unit 2 is used to apply light for subthreshold coagulation (aiming light, treatment light) to the retina Er of the patient's eye E via the optical fiber 3 and the probe 4. In addition to this, the optical unit 2 is used to apply an OCT scan to the retina Er via the optical fiber 3 and the probe 4.

Figure 2:
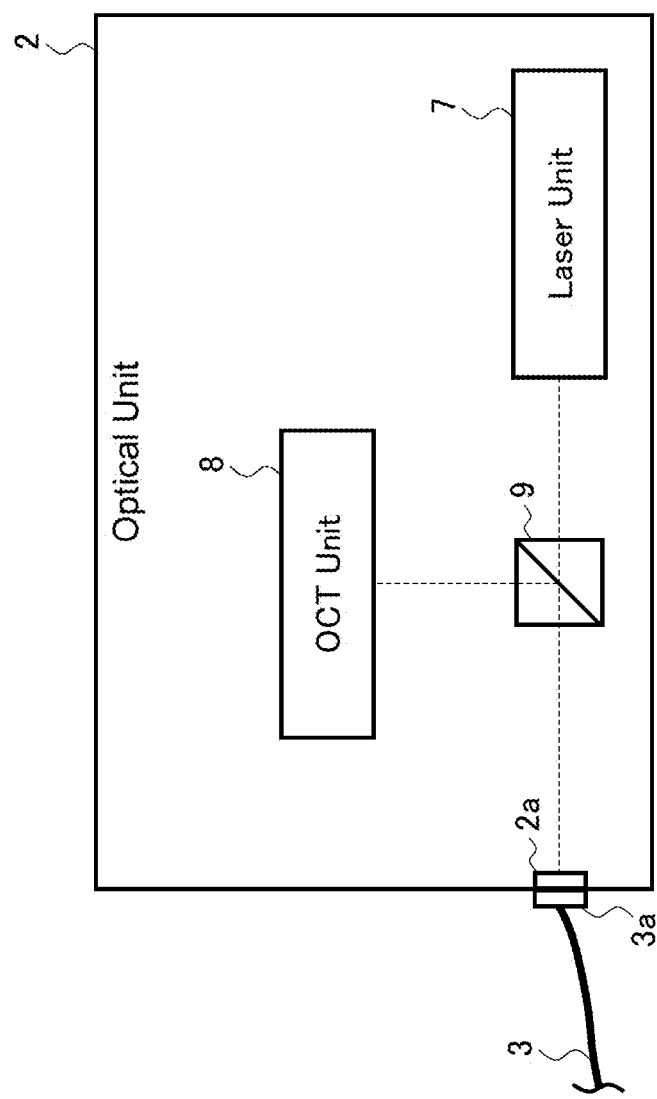
FIG. 2 is a schematic diagram illustrating the configuration of the photocoagulation apparatus according to the embodiment example.

FIG. 2 shows an example of the configuration of the optical unit 2. The optical unit 2 of the present example includes the laser unit 7 and the OCT unit 8. In addition, the optical unit 2 includes the beam splitter 9 that couples the optical path from the laser unit 7 and the optical path from the OCT unit 8. The beam splitter 9 may be, for example, a dichroic mirror or a half mirror.

The optical unit 2 has the adapter 2a. To the adapter 2a, the adapter 3a provided at the base end of the optical fiber 3 is connected. As a result of this, the optical unit 2 and the optical fiber 3 are optically connected. In addition to such optical connection, electrical connection or the like may be introduced.

The laser unit 7 includes an element to apply light for subthreshold coagulation to the retina Er. The laser unit 7 may have, for example, the same configurations as those of the embodiment example disclosed in Japanese Unexamined Patent Application Publication No. 2016-159070. The laser unit 7 includes an aiming light source and a treatment light source.

The aiming light source generates aiming light for aiming at a location where laser treatment (subthreshold coagulation) is to be applied. The aiming light contains, for example, one or both of a visible light component and an infrared light component, and at least contains a wavelength component included in a wavelength band that can be detected by the image sensor 33 described later. The aiming light contains, in the present embodiment example, at least a visible light component for observation through the observation system 20.

The treatment light source emits treatment laser light (treatment light). The treatment light may be visible laser light or invisible laser light depending on the intended use. In addition, the treatment light source may include a plurality of laser light sources or a single laser light source that emits laser light having different wavelengths.

The optical unit 2 includes a configuration for selectively outputting aiming light and treatment light. Further, in the case where two or more treatment light sources are provided, the optical unit 2 further includes a configuration for selectively outputting light from these treatment light sources.

The light (aiming light, treatment light) output from the laser unit 7 passes through the beam splitter 9 and enters the optical fiber 3 via the adapter 2a and the adapter 3a. The light incident on the optical fiber 3 is guided to the probe 4 through the optical fiber 3. The optical fiber 3 is connected to the base end of the probe 4. A part (including the tip) of the probe 4 is inserted into the patient's eye E through a hole formed in the sclera of the patient's eye E. The light guided to the probe 4 through the optical fiber 3 is emitted from the tip of the probe 4 and applied to the retina Er. Although not shown, other surgical instruments may be inserted into the eye.

The OCT unit 8 includes an element for applying an OCT scan to the retina Er. The OCT unit 8 includes, for example, an optical system for performing swept source OCT in the same manner as the OCT unit 100 described later with reference to FIG. 3. The optical system includes an interference optical system. The interference optical system splits light from a wavelength tunable light source into measurement light and reference light.

The measurement light is reflected by the beam splitter 9 and enters the optical fiber 3 via the adapter 2a and the adapter 3a. The measurement light having entered the optical fiber 3 is guided to the probe 4 through the optical fiber 3, exits from the tip of the probe 4, and then is projected onto the retina Er.

The return light of the measurement light projected on the retina Er is guided to the optical unit 2 via the probe 4, the optical fiber 3, the adapter 3a, and the adapter 2a. The return light having entered the optical unit 2 is reflected by the beam splitter 9 and then incident on the OCT unit 8. The OCT unit 8 superposes the return light of the measurement light with the reference light having traveled through the reference optical path, thereby yielding interference light. Then, the OCT unit 8 detects the interference light. The data (i.e., a detection signal, an interference signal) obtained by the detection of the interference light is a signal representing the spectrum of the interference light and is sent to the computer 200.

<Illumination System 10>

The illumination system 10 projects illumination light onto the fundus Ef of the patient's eye E. The illumination system 10 includes the illumination light source 11, the condenser lens 12, the illumination field diaphragm 13, the slit plate 14, the collimator lens 15, and the reflector 16.

The illumination light source 11 outputs illumination light. The illumination light contains, for example, one or both of a visible light component and an infrared light component, and at least contains a wavelength component included in a wavelength band that can be detected by the image sensor 33 described later. Typically, illumination light containing only an infrared light component is employed in order to avoid miosis during fundus observation. The illumination light output from the illumination light source 11 is refracted by the condenser lens 12 and guided to the illumination field diaphragm 13.

The illumination field diaphragm 13 is an optical member that limits a region onto which the illumination light is projected. The illumination field diaphragm 13 is provided at a position optically conjugate with the front focal point of the objective lens 21. The illumination light that has passed through the illumination field diaphragm 13 is guided to the slit plate 14.

The slit plate 14 is a light shielding plate in which a plurality of light transmitting parts (slits) are formed. The shapes of the plurality of slits correspond to the shape of the reflecting surface of the reflector 16. The slit plate 14 is driven (moved) by a mechanism that is not shown in the drawings, and the plurality of slits are selectively placed in the optical path. The slit placed in the optical path is arranged at a position optically conjugate with the front focal point of the objective lens 21. The illumination light that has passed through the slit is guided to the collimator lens 15.

The collimator lens 15 converts the illumination light that has passed through the slit into a parallel light beam. The illumination light that has become a parallel light beam is reflected by the reflecting surface of the reflector 16 and is projected onto the patient's eye E via the objective lens 21 (and the front lens 29). The return light (reflected light) of the illumination light projected onto the patient's eye E enters the observation system 20.

<Observation System 20>

The observation system 20 provides a magnified image of the patient's eye E to the user (doctor) via the eyepiece 28. Similar to the embodiment example disclosed in Japanese Unexamined Patent Application Publication No. 2016-206348, the observation system 20 has a pair of left and right optical systems (not shown in the drawings). The optical system on the left side provides a magnified image to the user's left eye, and the optical system on the right side provides a magnified image to the right eye. As a result, the user is able to observe a magnified stereoscopic image of the patient's eye E. Below, unless otherwise mentioned, a description will be given of one of the left and right optical systems.

The observation system 20 includes the objective lens 21 common to the left and right optical systems. Further, each of the left and right optical systems includes the zoom lens groups 22, 23 and 24, the beam splitter 25, the imaging lens 26, the image uprighting prism (Dove prism) 27, and the eyepiece 28. Each of the left and right optical systems may include an eye width adjusting prism and/or a visual field diaphragm as in the embodiment example disclosed in Japanese Unexamined Patent Application Publication No. 2016-206348.

The return light of the illumination light projected onto the patient's eye E is incident on the objective lens 21 (via the front lens 29). The return light refracted by the objective lens 21 is guided to the zoom lens groups 22, 23 and 24.

The zoom lens groups 22, 23 and 24 are relatively moved in the direction along the optical axis by a mechanism that is not shown in the drawings. With such a configuration, the magnification for observation or photography of the patient's eye E can be changed. The return light refracted by the zoom lens groups 22, 23 and 24 is directed to the beam splitter 25.

The beam splitter 25 splits the optical path of the photography system 30 from the optical path of the observation system 20. In other words, the beam splitter 25 couples the optical path of the observation system 20 and the optical path of the photography system 30. With this, part of the return light incident on the beam splitter 25 via the zoom lens groups 22, 23 and 24 is guided to the imaging lens 26, and another part of the return light is guided to the photography system 30.

The return light guided to the imaging lens 26 is directed to the image uprighting prism 27 after being subjected to the refraction action of the imaging lens 26. The image uprighting prism 27 converts the image (inverted image) formed by the imaging lens 26 into an upright image. The user may observe the upright image through the eyepiece 28.

In the case where the eye width adjusting prism mentioned above is provided, the distance between the left and right optical systems can be adjusted in accordance with the eye width (the distance between the left eye and the right eye) of the user. In addition, the visual field diaphragm mentioned above acts to limit the visual field of the user.

The front lens 29 is inserted in a position between the front focal point of the objective lens 21 and the patient's eye E at the time of observation of the fundus. In the case of anterior eye segment observation, the front lens 29 is removed from the optical path. Similar to the embodiment example disclosed in Japanese Unexamined Patent Application Publication No. 2016-206348, a plurality of front lenses that has mutually different refractive powers (e.g., 40 diopters, 80 diopters, 120 diopters) is prepared, and these front lenses are selectively used.

While the present embodiment example employs a Galilean stereo microscope, a Greenough stereo microscope may also be employed in some other embodiment examples. In a Galilean stereo microscope, the left and right optical systems are provided with a common objective lens and the left and right optical axes are arranged in parallel to each other. Meanwhile, the left and right optical systems are provided with separate objective lenses and the left and right optical axes are arranged in a non-parallel manner in a Greenough stereo microscope. An example of a Greenough stereo microscope employable in some embodiment examples can be found in the disclosure of Japanese Unexamined Patent Application Publication No. 2017-012431.

<Photography System 30>

The photography system 30 is capable of performing moving image photography of the retina Er of the patient's eye E. The photography system 30 includes the beam splitter 31, the imaging lens 32, and the image sensor 33. The image sensor 33 may be, for example, a charge-coupled device (CCD) image sensor or a complementary metal oxide semiconductor (CMOS) image sensor.

The return light guided to the optical path of the photography system 30 by the beam splitter 25 of the observation system 20 is directed to the beam splitter 31. The optical path of the OCT system 40 branches from the optical path of the photography system 30 via the beam splitter 31. In other words, the beam splitter 31 couples the optical path of the photography system 30 and the optical path of the OCT system 40 with each other. The beam splitter 31 is typically a dichroic mirror that reflects light of the wavelength band used in the OCT system 40 while transmitting light of the wavelength band used in the photography system 30. The return light guided to the imaging lens 32 is directed to the image sensor 33 after being subjected to the refraction action of the imaging lens 32. The image sensor 33 is capable of performing moving image photography at a predetermined photographing rate (frame rate). The photographing rate may be fixed or variable.

<OCT System 40>

The OCT system 40 applies an OCT scan to the retina Er of the patient's eye E. The OCT system 40 includes the OCT unit 100, the optical fiber 41, the collimator lens unit 42, the OCT focusing lens 43, and the optical scanner 44.

Figure 3:
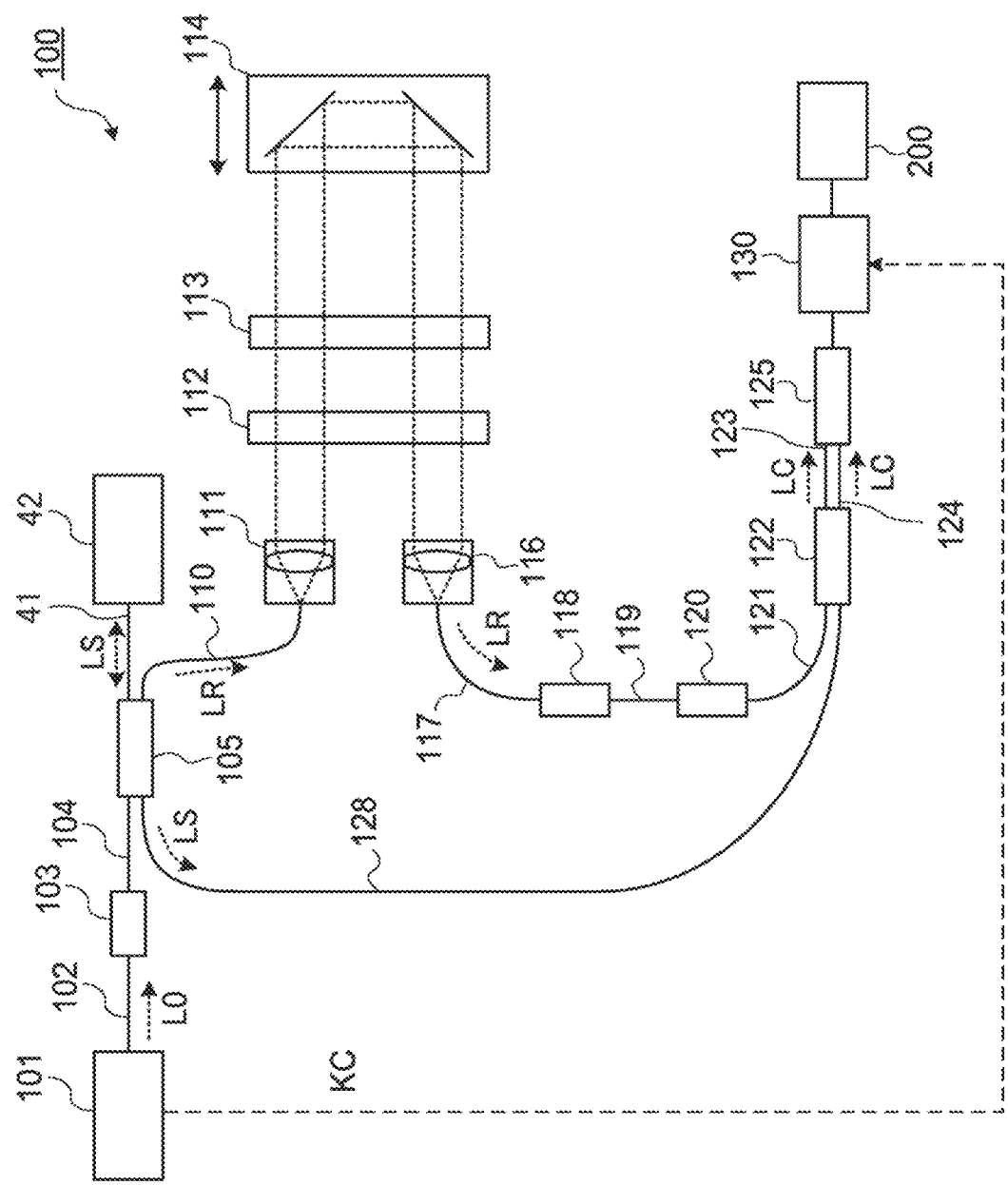
FIG. 3 is a schematic diagram illustrating the configuration of the photocoagulation apparatus according to the embodiment example.

The exemplary OCT unit 100 shown in FIG. 3 is provided with the optical system for performing swept source OCT. The optical system includes an interference optical system. The interference optical system is configured to split light emitted from a wavelength tunable light source into measurement light and reference light, superpose the return light of the measurement light projected onto the patient's eye E with the reference light having traveled through the reference optical path, thereby yielding interference light. Then, the interference optical system detects the interference light. The data (i.e., a detection signal, an interference signal) obtained by detecting the interference light is a signal representing the spectrum of the interference light and is sent to the computer 200.

The light source unit 101 includes, for example, a near-infrared wavelength tunable laser configured to vary wavelengths of emitted light at high speed. The low coherence light LO output from the light source unit 101 is guided to the polarization device 103 through the optical fiber 102, and the polarization state of the light LO is regulated. Further, the light LO with regulated polarization state is guided to the fiber coupler 105 through the optical fiber 104 and is split into the measurement light LS and the reference light LR. The optical path of the measurement light LS is referred to as a measurement arm, and the optical path of the reference light LR is referred to as a reference arm.

The reference light LR generated by the fiber coupler 105 is guided through the optical fiber 110 to the collimator lens 111, is converted into a parallel light beam, travels through the optical path length correction member 112 and the dispersion compensation member 113, and is guided to the retroreflector 114. The optical path length correction member 112 acts to match the optical path length of the reference light LR and that of the measurement light LS with each other. The dispersion compensation member 113 acts to eliminate the difference between the dispersion characteristics of the reference light LR and that of the measurement light LS. The retroreflector 114 is movable along the optical path of the reference light LR incident on the retroreflector 114. With this, the length of the reference arm is changed. The change in the length of the reference arm may be utilized for operations such as optical path length correction according to axial length and interference condition adjustment.

After passing through the retroreflector 114, the reference light LR travels through the dispersion compensation member 113 and the optical path length correction member 112, is converted from a parallel light beam to a convergent light beam by the collimator lens 116, and is incident on the optical fiber 117. The reference light LR having entered the optical fiber 117 is guided to the polarization device 118, and the polarization state of the reference light LR is regulated. Then, the reference light LR is guided to the attenuator 120 through the optical fiber 119, and the light amount of the reference light LR is regulated. Subsequently, the reference light LR is guided to the fiber coupler 122 through the optical fiber 121.

Meanwhile, the measurement light LS generated by the fiber coupler 105 is guided to the collimator lens unit 42 through the optical fiber 41 and is converted to a parallel light beam. Then, the measurement light LS passes through the OCT focusing lens 43 and the optical scanner 44, and then is reflected by the beam splitter 31. Subsequently, the measurement light LS is reflected by the beam splitter 25 and is projected onto the patient's eye E via the zoom lens groups 24, 23, and 22, as well as the objective lens 21 (and further, the front lens 29).

The measurement light LS is reflected and scattered at various depths of the patient's eye E. The return light of the measurement light LS returning from the patient's eye E travels along the measurement arm in the opposite direction to the measurement light LS projected onto the patient's eye E, is directed to the fiber coupler 105, and then is directed to the fiber coupler 122 via the optical fiber 128.

The fiber coupler 122 superposes the measurement light LS incident through the optical fiber 128 with the reference light LR incident through the optical fiber 121, to generate interference light. The fiber coupler 122 splits the generated interference light at a predetermined splitting ratio (e.g., 1 to 1) to generate a pair of interference light LC. The pair of interference light LC is guided to the detector 125 through the optical fibers 123 and 124, respectively.

The detector 125 includes, for example, a balanced photo diode. The balanced photodiode includes a pair of photodetectors for respectively detecting the pair of the interference light LC. The balanced photodiode outputs a difference between a pair of detection signals corresponding to the pair of the interference light LC respectively obtained by the pair of photodetectors. The detector 125 sends the output (difference signal) to the data acquisition system (DAQ) 130.

The clock KC is supplied from the light source unit 101 to the data acquisition system 130. The clock KC is generated in the light source unit 101 in synchronization with the output timings of wavelengths varied over a predetermined wavelength range by the wavelength tunable type light source. For example, the light source unit 101 is configured to split the light LO of each output wavelength to generate two pieces of split light, apply an optical delay to one of the two pieces of split light, combine the resulting two pieces of split light, detect the combined light, and generate the clock KC based on the detection signal of the combined light. The data acquisition system 130 performs sampling of the signal (difference signal) input from the detector 125 based on the clock KC. The data acquisition system 130 sends the data obtained by the sampling to the computer 200.

In general, an ophthalmic OCT apparatus is provided with an element for changing the difference between the measurement arm length and the reference arm length (i.e., optical path length difference) in order to move the coherence gate in the depth direction (axial direction). While an element for changing the reference arm length (the retroreflector 114 or a reference mirror) is provided in the present example, an element for changing the measurement arm length may be employed in some other examples.

The OCT focusing lens 43 is moved in the direction along the measurement arm to conduct focus adjustment of the measurement arm (that is, to change the focal position of the measurement arm).

The optical scanner 44 is placed at a position substantially optically conjugate with respect to the pupil of the patient's eye E when the front lens 29 is inserted in the optical path. The optical scanner 44 is configured to deflect the measurement light LS guided through the measurement arm. An example of the optical scanner 44 is provided by a galvano scanner configured to be capable of two dimensional scanning. Typically, the optical scanner 44 includes a one dimensional scanner for deflecting the measurement light LS in the first direction (+x and −x directions), and another one dimensional scanner for deflecting the measurement light LS in the second direction orthogonal to the first direction (+y and −y directions). The former may be referred to as an x-scanner and the latter as a y-scanner. When such a configuration is employed, for example, either one of the x-scanner and the y-scanner may be placed at the optically conjugate position described above. Alternatively, the optically conjugate positions may be placed at a location between the x-scanner and the y-scanner.

<Computer 200>

The computer 200 controls each part (each element) of the photocoagulation apparatus 1. Further, the computer 200 executes various kinds of data processing.

The computer 200 includes, for example, a processor, a random access memory (RAM), a read only memory (ROM), a hard disk drive, and a communication interface. A storage such as the hard disk drive stores various kinds of computer programs. The computer programs are executed by the processor of the computer 200. The computer 200 may include an operation device, an input device, a display device, etc.

Note that the "processor" as used in the present disclosure is hardware for executing a set of commands described in a software program. Such a processor typically includes an arithmetic unit, a resistor, a peripheral circuit, and the like. For example, the processor refers to a circuit or an electrical circuit configuration (or circuitry) such as a central processing unit (CPU), a graphics processing unit (GPU), a microprocessing unit (MPU), a digital signal processor (DSP), an application specific integrated circuit (ASIC), a programmable logic device (e.g., a simple programmable logic device (SPLD), a complex programmable logic device (CPLD), or a field programmable gate array (FPGA)), or the like. For example, the processor loads a program stored in storage hardware (e.g., a memory circuit or a storage), and executes the program, thereby implementing the functions according to a corresponding embodiment example. The processor may include at least part of the storage hardware.

The computer 200 may include a user interface (not shown in the drawings). The user interface includes a display part and an operation part. The display part may include the display device 300. The operation part includes various kinds of operation devices and input devices. The user interface may include a device having both the display function and the operation function, such as a touch panel display.

<Processing System>

Figure 4:
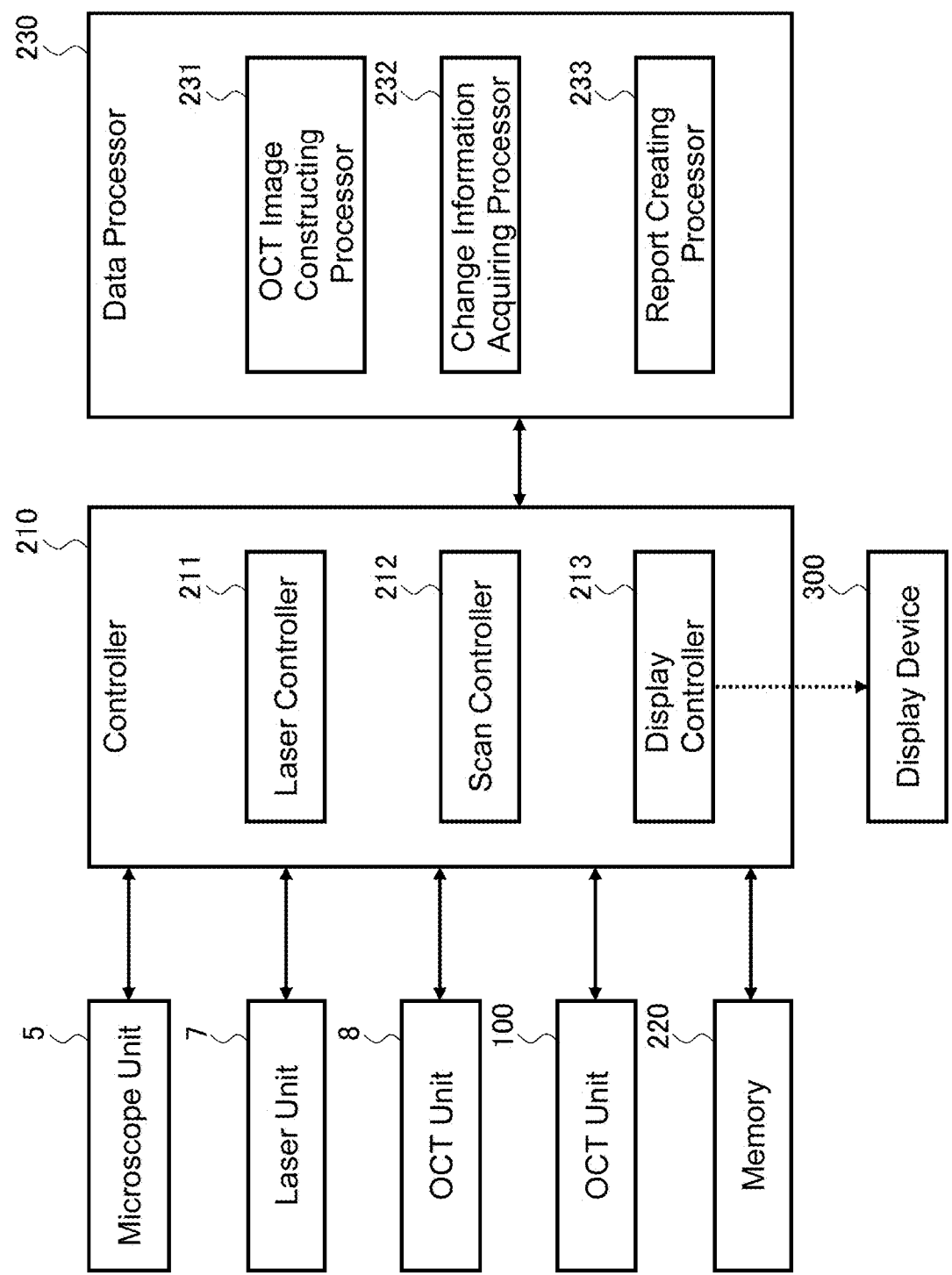
FIG. 4 is a schematic diagram illustrating the configuration of the photocoagulation apparatus according to the embodiment example.

FIG. 4 shows a configuration example of the processing system of the photocoagulation apparatus 1. The controller 210, the memory 220, and the data processor 230 are provided in the computer 200. The microscope unit 5 includes the illumination system 10, the observation system 20, and the photography system 30.

<Controller 210>

The controller 210 controls each element of the photocoagulation apparatus 1 (including the elements shown in FIG. 1 to FIG. 4). The controller 210 includes a processor and a storage. The functions of the controller 210 may typically be implemented by the cooperation of hardware including a processor and software including a control program. At least part of the functions of the controller 210 may be implemented by means of hardware including a control circuit.

The controller 210 includes the laser controller 211, the scan controller 212, and the display controller 213.

<Laser Controller 211>

The laser controller 211 is configured to control the laser unit 7. The laser controller 211 performs control of the aiming light source and the treatment light source described above. For example, the laser controller 211 performs control of turning on and off of output and control of the output intensity (output power). In the case of employing a configuration capable of outputting a plurality of types of treatment light by using one or more treatment light sources, the laser controller 211 performs control to selectively output the plurality of types of treatment light.

<Scan Controller 212>

The scan controller 212 performs control related to OCT scanning performed using the OCT unit 8 and control related to OCT scanning performed using the OCT system 40.

As the control related to OCT scanning performed using the OCT unit 8, the scan controller 212 performs control of a light source (e.g., a wavelength tunable light source, etc.) in the OCT unit 8, control to change an arm length, and the like. Note that an OCT scan performed using the OCT unit 8 is typically an A-scan, that is, a one dimensional scan along the axial direction without lateral scanning. The axial direction is referred to as an A-line. In addition, the probe 4 may be provided with an element for performing lateral scanning in order to enable execution of a B-scan, a three dimensional scan, or the like.

As the control related to OCT scanning performed using the OCT system 40, the scan controller 212 performs control of the light source unit 101, control of the optical scanner 44 (i.e., control for lateral scanning), control to change an arm length, and the like. The scan controller 212 at least applies an OCT scan to the retina Er by combining the control of the light source unit 101 and the optical scanner 44. Details of controls executable by the scan controller 212 will be described later.

<Display Controller 213>

The display controller 213 is configured to display various kinds of information on the display device 300. In addition, the display controller 213 may perform various kinds of data processing relating to information to be displayed. The details of the control that can be executed by the display controller 213 will be described later.

<Memory 220>

The memory 220 stores various kinds of data. Further, the memory 220 stores various kinds of software, various kinds of parameters, and various kinds of templates for operating the photocoagulation apparatus 1.

The memory 220 of the present embodiment example may store an OCT image of the retina Er in advance. The OCT image is referred to as a reference OCT image. The reference OCT image is a three dimensional image of the fundus Ef that represents at least a three dimensional region of the retina Er. Typically, the reference OCT image is a wide area OCT image obtained by applying an OCT scan over a wide area of the retina Er. The wide area OCT image may be an image obtained by a wide angle OCT scan or a mosaic image obtained by a panoramic OCT scan. The panoramic OCT scan is a scan mode in which an OCT scan is sequentially applied to a plurality of regions of the fundus Ef, and the mosaic image is an image constructed by pasting together a plurality of OCT images respectively corresponding to the plurality of regions of the fundus Ef.

A reference OCT image may be prepared in the case where an OCT scan is performed only after application of laser to the retina Er (an OCT scan is not performed before laser application). The reference OCT image may be acquired before the current laser treatment, or may be acquired during a period from the commencement of the current laser treatment to actual laser application. As an example of the latter, a reference OCT image may be acquired using the OCT system 40 before the first laser application during the current laser treatment.

The memory 220 of the present embodiment example stores a template of treatment reports in advance. A treatment report is a document (report) on the photocoagulation treatment having been conducted. In the present embodiment example, a treatment report is created by entering information in a template of a default format. Such a template is being stored in the memory 220.

The memory 220 typically includes a storage having a relatively large capacity such as a hard disk. Note that various kinds of data may be stored in a storage or an information processing apparatus located on a communication line. If this is the case, the memory 220 does not need to include the storage having a relatively large capacity. The same applies if a relatively large capacity storage is employed as a peripheral device of the photocoagulation apparatus 1.

<Data Processor 230>

The data processor 230 performs various kinds of data processing. For example, the data processor 230 may be configured to construct OCT image data, apply image processing and/or analysis processing to OCT image data, and/or, apply image processing and/or analysis processing to observation image data or photographed image data.

The function of the data processor 230 may typically be implemented by the cooperation of hardware including a processor and software including a data processing program. At least part of the function of the data processor 230 may be implemented by hardware including a data processing circuit.

The data processor 230 includes the OCT image constructing processor 231, the change information acquiring processor 232, and the report creating processor 233.

<OCT Image Constructing Processor 231>

The OCT image constructing processor 231 is configured to construct OCT image data from data acquired by the OCT unit 8. In addition to this, the OCT image constructing processor 231 constructs OCT image data from data acquired by the OCT unit 100. While the image data construction process of the latter will be mainly described below, the image data construction process of the former is also executed in the same manner.

Typically, the OCT image constructing processor 231 constructs cross sectional image data based on data acquired by the data acquisition system 130 of the OCT unit 100. The image construction processing includes signal processing such as noise elimination (noise reduction), filtering, fast Fourier transform (FFT), and other processes as in conventional swept source OCT.

For example, the OCT image constructing processor 231 applies signal processing such as Fourier transform on the spectral distribution based on a sampling data group collected by the data acquisition system 130 for each series of wavelength scanning (for each A-line). This constructs reflection intensity profiles respectively for A-lines. Furthermore, the OCT image constructing processor 231 applies imaging processing to the reflection intensity profiles for the A-lines to construct image data. Arithmetic processes for the image data construction are the same as those of conventional swept source OCT.

Image data constructed by the OCT image constructing processor 231 is a data set including a group of a plurality of pieces of image data obtained by applying imaging processing to reflection intensity profiles at corresponding A-lines arranged in the area to which an OCT scan is applied.

An OCT scan applied to an A-line is referred to as an A-scan. Image data obtained by an A-scan is called A-scan image data. Further, the direction along the A-line is referred to as the A-scan direction. A collection of a plurality of A-scans arranged in a one dimensional direction orthogonal to the A-scan direction is referred to as a B-scan. The one dimensional direction orthogonal to the A-scan direction is referred to as the B-scan direction. Image data obtained by a B-scan is referred to as B-scan image data. B-scan image data is two dimensional cross sectional image data.

Image data constructed by the OCT image constructing processor 231 is, for example, one or more pieces of A-scan image data, one or more pieces of B-scan image data, or three dimensional image data. Three dimensional image data is image data represented by a three dimensional coordinate system, and typical examples thereof include stack data and volume data. Stack data is constructed by embedding a plurality of pieces of B-scan image data in a single three dimensional coordinate system. Volume data, also referred to as voxel data, is constructed by applying voxelization processing to stack data.

Note that the probe 4 of the present embodiment example does not have a function of lateral scanning: therefore, A-scan image data is constructed from data acquired by the OCT unit 8. However, image data constructed from data acquired by the OCT unit 8 is not limited to A-scan image data in some embodiment examples in which a probe capable of lateral scanning is employed. Image data constructed from data acquired by the OCT unit 8 in such embodiment examples may be image data according to the scan mode (for example, B-scan image data, three dimensional image data).

The OCT image constructing processor 231 may be configured to apply image processing to image data using any known image processing technique. For example, the OCT image constructing processor 231 may construct new image data by applying rendering to three dimensional image data. Examples of the rendering method include volume rendering, maximum intensity projection (MIP), minimum intensity projection (MinIP), surface rendering, and multi planar reconstruction (MPR). Further, the OCT image constructing processor 231 may be configured to construct projection data by projecting three dimensional image data in the A-line direction. In addition, the OCT image constructing processor 231 may be configured to construct a shadowgram by projecting part of three dimensional image data in the A-line direction. Here, the part of the three dimensional image data projected for the shadowgram construction is extracted by using segmentation, for example.

<Change Information Acquiring Processor 232>

The change information acquiring processor 232 is configured to acquire, from two or more OCT images acquired at different times (different time points), change information representing a tissue change in the retina Er caused by the treatment light. The change information includes, for example, any of the following types of information: a position (location) where a tissue change has occurred, a distribution of positions (locations) where tissue changes have occurred, and the size (magnitude), shape, and degree of a tissue change.

The OCT unit 8 of the present embodiment example may apply an OCT scan at both time points before and after the application of the treatment light on the retina Er. In other words, the photocoagulation apparatus 1 may carry out the following processes in this order: an OCT scan targeted to a location where the treatment light is to be applied (the OCT scan is an A-scan performed using the OCT unit 8); application of the treatment light to that location; and another OCT scan targeted to the location on which the treatment light has been projected (this OCT scan is also an A-scan performed using the OCT unit 8).

If this is the case, the change information acquiring processor 232 may perform a comparison between the first OCT image and the second OCT image. The first OCT image is an OCT image constructed based on data acquired by the OCT scan, which is the A-scan performed using the OCT unit 8 as mentioned above, before the treatment light application. The second OCT image is an OCT image constructed based on data acquired by the OCT scan, which is also the A-scan performed using the OCT unit 8 as mentioned above, after the treatment light application. With such comparison between the first and second OCT images, the change information acquiring processor 232 may identify a tissue change at the location caused by the treatment light and then generate change information including a result of the tissue change identification.

In the case where the memory 220 of the present embodiment example stores a reference OCT image (typically, a wide area three dimensional image), the photocoagulation apparatus 1 may perform an OCT scan only after the treatment light application to the retina Er without performing an OCT scan before the treatment light application.

If this is the case, the change information acquiring processor 232 may execute a comparison between the reference OCT image (the first OCT image) and an OCT image (the second OCT image). Here, the second OCT image is constructed based on data acquired by the OCT scan performed after the treatment light application (the OCT scan is an A-scan performed using the OCT unit 8). With the comparison, the change information acquiring processor 232 may identify a tissue change, caused by the treatment light, at the location to which the treatment light has been applied, and then generate change information including a result of the tissue change identification.

Furthermore, the change information acquiring processor 232 may execute a comparison between any one of the first OCT images described above and the third OCT image. The third OCT image is constructed based on data acquired by the OCT scan performed after the completion of the current photocoagulation treatment. The OCT scan for obtaining the third OCT image is a three dimensional scan performed using the OCT unit 100, and the third OCT image is a three dimensional image. With the comparison, the change information acquiring processor 232 may identify tissue changes in the retina Er caused by the current photocoagulation treatment (subthreshold coagulation on a plurality of locations of the retina Er), and then generate change information including a result of the tissue change identification.

In addition, the change information acquiring processor 232 may execute a comparison between the second OCT image and the third OCT image. The second OCT image is constructed based on data acquired by the OCT scan performed after the application of the treatment light to a certain location in the retina Er. The OCT scan for obtaining the second OCT image is an A-scan performed using the OCT unit 8. The third OCT image is constructed based on data acquired by the OCT scan after the completion of the current photocoagulation treatment. The OCT scan for obtaining the third OCT image is a three dimensional scan performed using the OCT unit 100, and the third OCT image is a three dimensional image. With the comparison between the second OCT image and the third OCT image, the change information acquiring processor 232 may compare an initial tissue change caused by the treatment light applied to that location and a subsequent tissue change with each other, and then generate change information including a result of the tissue change comparison. In other words, the change information acquiring processor 232 may be capable of acquiring change information representing a time course of a tissue change caused by the treatment light.

In some examples, the change information acquiring processor 232 may be configured to obtain a tissue change in the retina Er, for example, by executing the series of processes as follows.

First, the change information acquiring processor 232 performs, if necessary, position matching (registration) between two or more OCT images acquired at different times (different time points) from substantially the same position (substantially the same location) of the retina Er.

In the case of employing the reference OCT image (three dimensional image) as a reference, the change information acquiring processor 232 identifies a position in the reference OCT image that corresponds to the application position of the treatment light. In order to perform the application position identification, the change information acquiring processor 232 first extracts an image of the aiming light from a front image of the retina Er acquired by the photography system 30 at a time point immediately before the application of the treatment light. Further, the change information acquiring processor 232 performs registration between the front image and an OCT front image. The OCT front image is a projection image constructed from the reference OCT image (which is a three dimensional image) by the OCT image constructing processor 231. The registration enables the identification of the position in the OCT front image that corresponds to the position of the image of the aiming light in the front image. Note that a typical aspect performs an OCT scan immediately after the application of the treatment light: therefore, the position of the aiming light immediately before the application of the treatment light and the application position of the OCT scan immediately after the application of the treatment light may be considered substantially the same. The position identification may be carried out in the same manner as the above registration (i.e., the registration between the front image and the OCT front image) in the case where no OCT scan is applied immediately after the application of the treatment light.

In the case where an OCT scan (A-scan) is applied both before and after the application of the treatment light, typically, the treatment light is applied immediately after the OCT scan before application of the treatment light and then an OCT scan is performed immediately after this application of the treatment light. Therefore, the application position of the OCT scan before the application of the treatment light and the application position of the OCT scan immediately after the application of the treatment light may be considered to be substantially the same. Note that the position identification may be carried out by using the registration described above (i.e., the registration between the front image and the OCT front image) in the case where no treatment light is applied immediately after the OCT scan before the application of the treatment light, or in the case where no OCT scan is applied immediately after the application of the treatment light.

After performing the registration as needed, the change information acquiring processor 232 constructs an image representing a change between these OCT images by calculating a difference between or a ratio of two or more OCT images (to which the registration has been applied).

As a specific example, first, the change information acquiring processor 232 may construct motion contrast data from two or more OCT images (to which the registration has been conducted). Subsequently, the change information acquiring processor 232 may obtain a tissue change in the retina Er from the motion contrast data constructed. A method or technique for constructing motion contrast data is known, and is disclosed in, for example, Japanese Unexamined Patent Application Publication No. 2015-131107 and Japanese Unexamined Patent Application Publication No. 2016-010656.

<Report Creating Processor 233>

The report creating processor 233 reads out a template of a treatment report from the memory 220 and enters data in the template based on the information acquired by the change information acquiring processor 232.

The template is provided with input fields (entry fields) corresponding to various kinds of input items (entry items). As described above, the change information acquiring processor 232 acquires information on various kinds of items such as a position where a tissue change has occurred, a distribution of such positions, the size of a tissue change, the shape of a tissue change, and the degree of a tissue change, and the like. The report creating processor 233 then identifies a correspondence relationship between the items of information acquired by the change information acquiring processor 232 and the items in the template. Subsequently, the report creating processor 233 identifies a field in the template into which corresponding information is to be entered, and then enters the corresponding information in the field identified.

The report creating processor 233 may input data into the template based on information other than the information acquired by the change information acquiring processor 232. For example, the report creating processor 233 may enter, in the template, an image acquired by the photography system 30, an image acquired by the OCT system 40, information input by the user (doctor), or the like. In addition, the user may delete or edit the data that has been entered by the report creating processor 233.

<Usage Mode>

Some usage modes of the photocoagulation apparatus 1 will be described.

<First Usage Mode>

Figure 5A:
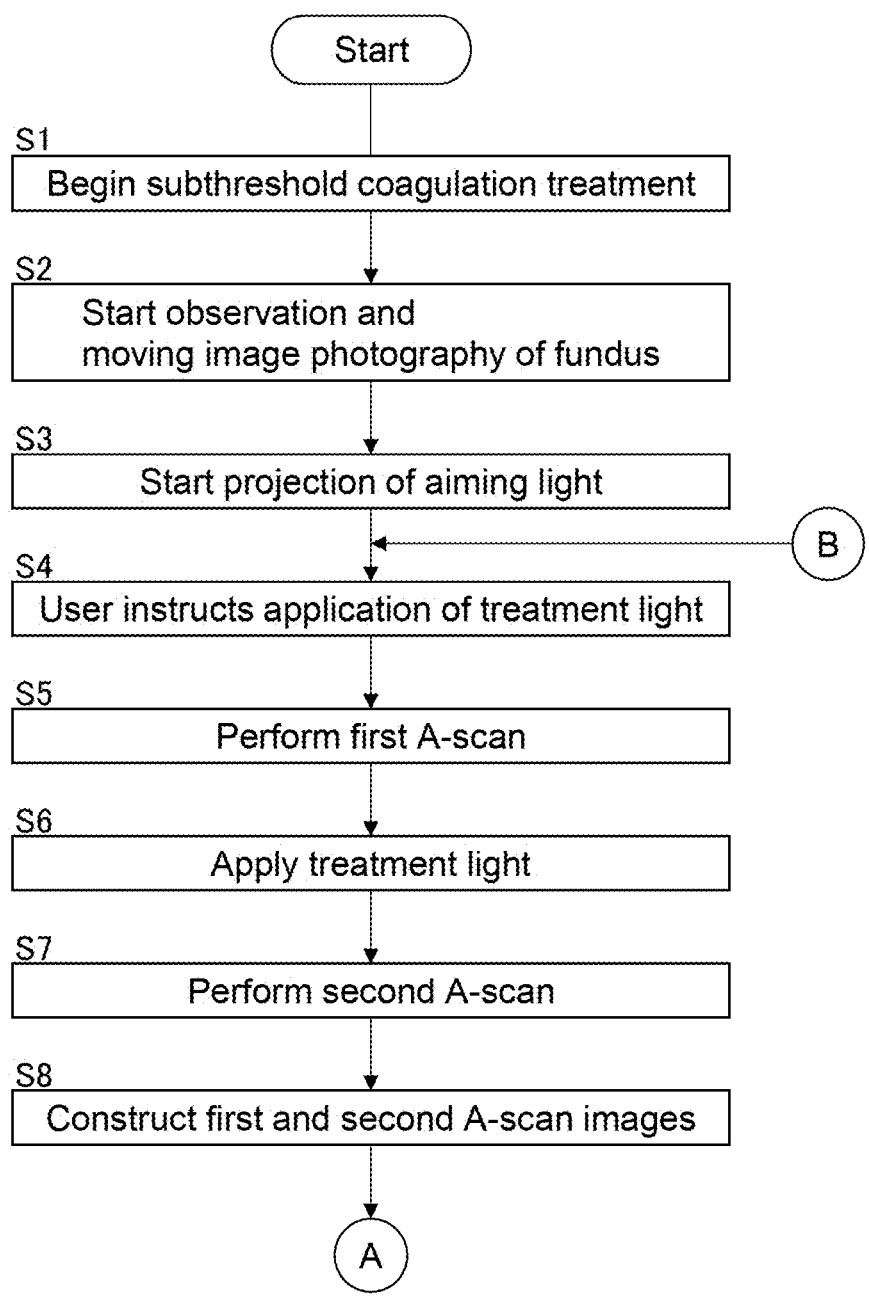
FIG. 5A is a flowchart illustrating a usage mode of the photocoagulation apparatus according to the embodiment example.
Figure 5B:
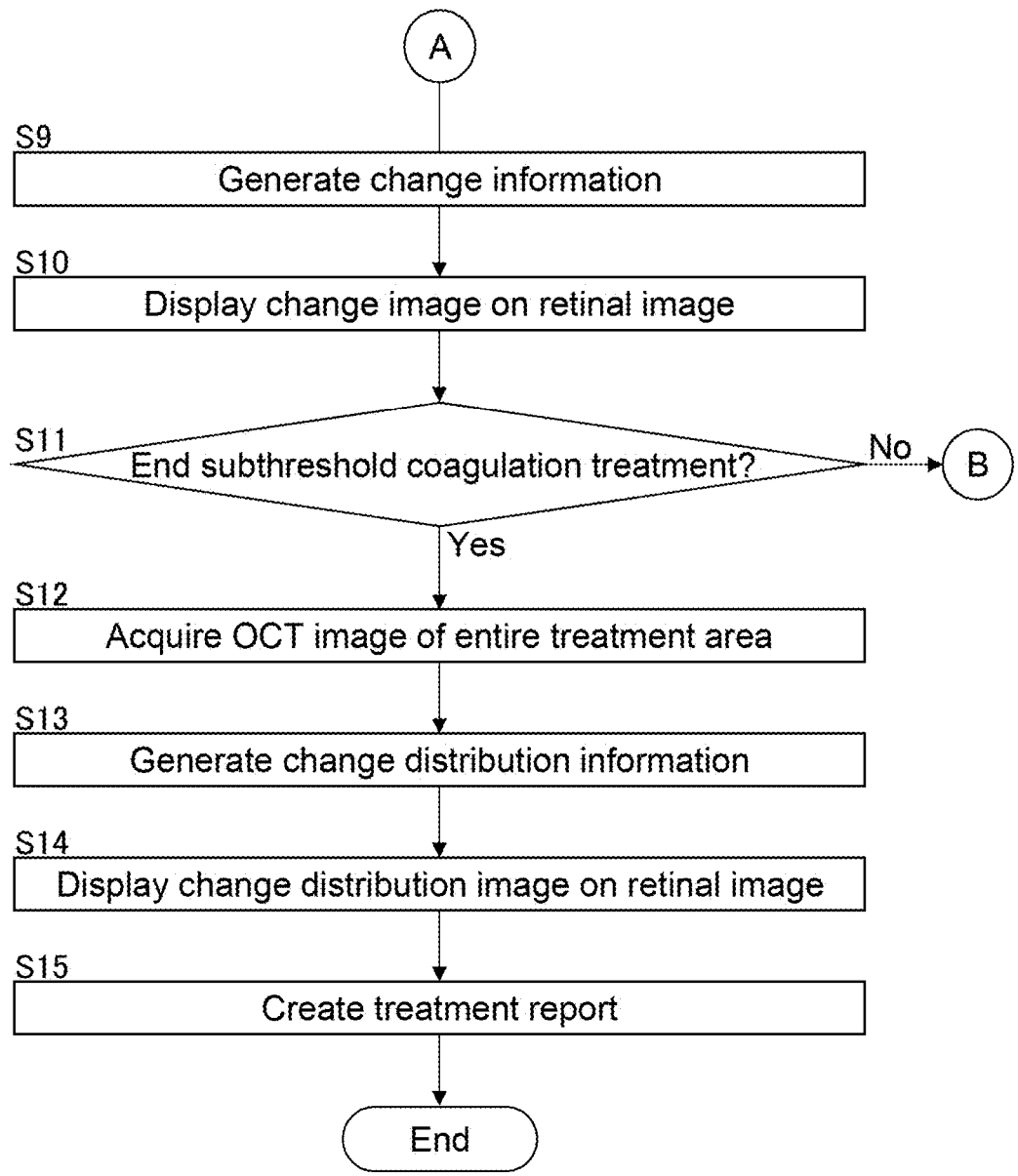
FIG. 5B is a flowchart illustrating a usage mode of the photocoagulation apparatus according to the embodiment example.

FIG. 5A and FIG. 5B show the flow of a usage mode example. The present example performs an OCT scan both before and after the application of the treatment light.

Prior to the commencement of subthreshold coagulation treatment, the photocoagulation apparatus 1 may perform acquisition of a retinal image. Note that the photocoagulation apparatus 1 may acquire a retinal image at an arbitrary time after the commencement of subthreshold coagulation treatment. The retinal image thus acquired is stored in the memory 220.

The retinal image is acquired by the photocoagulation apparatus 1 or another ophthalmic imaging apparatus. Examples of the retinal image that can be acquired by the photocoagulation apparatus 1 of the present embodiment example include an image of the retina Er acquired by the photography system 30 and a front image of the retina Er acquired by the OCT system 40 and the OCT image constructing processor 231.

More generally, the retinal image may be any of the following: (1) an image of the retina Er acquired by a fundus camera, such as a gray scale image, a color image, a morphological image, and a fluorescent contrast image: (2) an image of the retina Er acquired by a scanning laser ophthalmoscope (SLO), such as a gray scale image, a color image, a morphological image, and a fluorescent contrast image: (3) an image of the retina Er acquired by a surgical microscope: (4) an image of the retina Er acquired by a slit lamp microscope: (5) a front image of the retina Er acquired by using OCT, such as a morphological image and a blood vessel emphasized image (also referred to as an OCT angiogram and a motion contrast image).

(S1: Begin Subthreshold Coagulation Treatment)

The user (doctor) conducts predetermined preparatory operations such as activation of the photocoagulation apparatus 1 and insertion of the probe 4 into the patient's eye E. Then, the user begins subthreshold coagulation treatment.

(S2: Start Observation and Moving Image Photography of Fundus)

In response to an instruction for beginning the subthreshold coagulation treatment, the controller 210 turns on the illumination light source 11 of the illumination system 10 and activates the image sensor 33. As a result, observation of the fundus Ef (the retina Er) using the observation system 20 may be started, and moving image photography of the fundus Ef (the retina Er) by the photography system 30 may be started.

(S3: Start Projection of Aiming Light)

In response to the user performing a predetermined operation, the controller 210 controls the optical unit 2 to start the output of the aiming light.

(S4: User Instructs Application of Treatment Light)

The user issues an instruction to start application of treatment light while the aiming light is being projected onto a desired location on the retina Er. The instruction is issued, for example, by operating an application button or a foot switch (not shown in the drawings).

(S5: Perform First A-Scan)

The scan controller 212 receives the instruction for treatment light application and then controls the OCT unit 8 to perform an OCT scan on the retina Er.

In this OCT scan, the measurement light output from the OCT unit 8 is applied, via the optical fiber 3 and the probe 4, to the projection position of the aiming light at the time of the application instruction of the treatment light being issued in the step S4. The return light of the measurement light (part of the return light) enters the optical unit 2 via the probe 4 and the optical fiber 3 and is then guided to the OCT unit 8. The OCT unit 8 superposes the return light of the measurement light with the reference light, thereby yielding interference light. Then, the OCT unit 8 detects the interference light and acquires detection data. The detection data acquired is sent to the OCT image constructing processor 231.

Figure 6A:
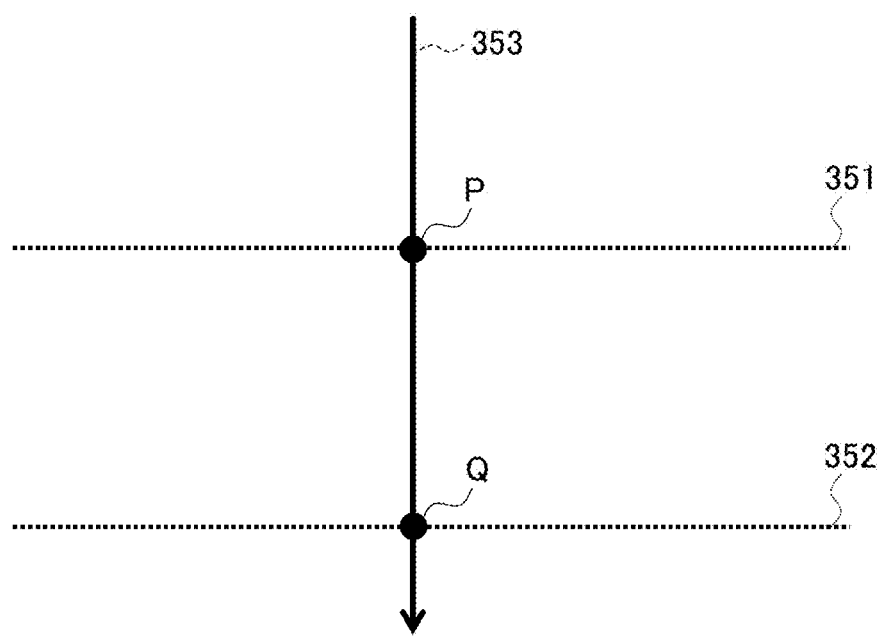
FIG. 6A is a schematic diagram for describing a usage mode of the photocoagulation apparatus according to the embodiment example.

FIG. 6A shows an overview of the OCT scan performed in the present step. The reference character 351 denotes the surface of the retina Er (e.g., the inner limiting membrane), and the reference character 352 denotes the retinal pigment epithelium. Further, the reference character P denotes the aiming position that is the projection position of the aiming light at the time of the application instruction of the treatment light being issued in the step S4, and the reference character Q denotes the position in the retinal pigment epithelium 352 located below the aiming position. In addition to this, the reference character 353 denotes the OCT scan of the present step. The OCT scan 353 is an A-scan performed in such a way that the A-scan passes through both the aiming position P located on the surface of the retina Er and the position Q located in the retinal pigment epithelium 352 (referred to as the first A-scan).

(S6: Apply Treatment Light)

The laser controller 211 controls the laser unit 7 to output treatment light immediately after the first A-scan in the step S5 is executed. The treatment light output is applied to the retina Er via the optical fiber 3 and the probe 4.

Figure 6B:
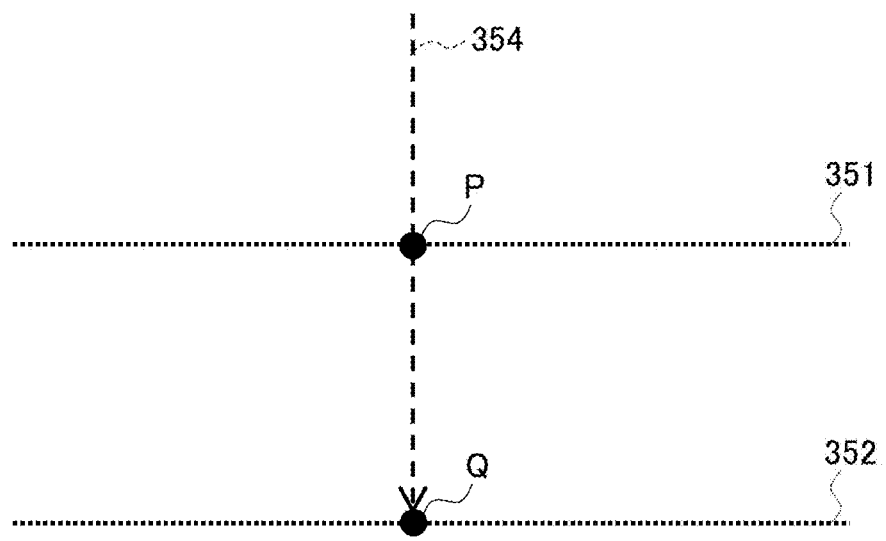
FIG. 6B is a schematic diagram for describing a usage mode of the photocoagulation apparatus according to the embodiment example.
Figure 6C:
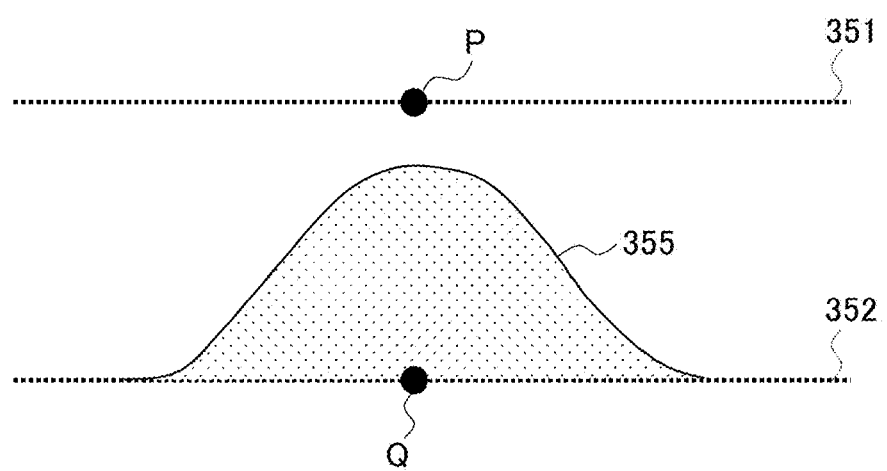
FIG. 6C is a schematic diagram for describing a usage mode of the photocoagulation apparatus according to the embodiment example.

FIG. 6B shows an overview of the application of the treatment light in the present step. The reference character 354 denotes the path of the treatment light. The treatment light passes through the aiming position P located on the retina Er and then is applied to the position Q located in the retinal pigment epithelium 352. The energy of the treatment light is absorbed by the retinal pigment epithelium 352 and converted to heat. The heat changes (destroys, damages) the retinal pigment epithelium 352 and a retinal tissue over the retinal pigment epithelium 352. The reference character 355 in FIG. 6C denotes an area in which the retinal tissue is changed by the energy of the treatment light (referred to as a change area). Note that the change area does not reach the surface of the retina Er since the present embodiment example employs subthreshold coagulation. Therefore, the change area 355 cannot be seen by using the observation system 20 or the photography system 30.

Here, an application condition(s) of the treatment light may be stored in the memory 220. Examples of the application condition include wavelength, intensity, application time, spot size, duty ratio (or duty cycle), and pulse width.

(S7: Perform Second A-Scan)

The scan controller 212 controls the OCT unit 8 to perform another OCT scan on the retina Er immediately after the application of the treatment light in the step S6. The OCT scan is performed in the same manner as the OCT scan of the step S5.

Figure 6D:
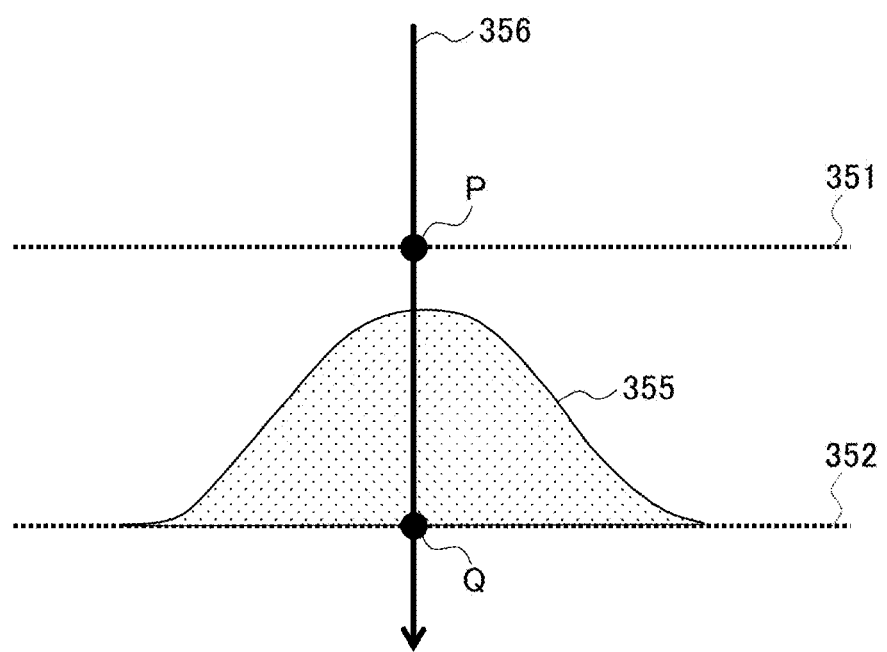
FIG. 6D is a schematic diagram for describing a usage mode of the photocoagulation apparatus according to the embodiment example.

FIG. 6D shows an overview of the OCT scan performed in the present step. The reference character 356 denotes the OCT scan of the present step. The OCT scan 356 is an A-scan performed in such a way that the A-scan passes through the aiming position P located on the surface of the retina Er and the position Q located in the retinal pigment epithelium 352 (referred to as the second A-scan).

Thus, the present example applies the first A-scan to the retina Er before the application of the treatment light and also applies the second A-scan to the retina Er whose tissue has been changed by the treatment light.

(S8: Construct Respective First and Second A-Scan Images)

The OCT image constructing processor 231 constructs an A-scan image from data acquired by the first A-scan performed in the step S5 (referred to as the first A-scan image), and also constructs another A-scan image from data acquired by the second A-scan performed in the step S7 (referred to as the second A-scan image).

(S9: Generate Change Information)

The change information acquiring processor 232 generates change information representing a tissue change in the retina Er caused by the treatment light applied in the step S6, by comparing the first A-scan image and the second A-scan image respectively constructed in the step S8 with each other.

Figure 6E:
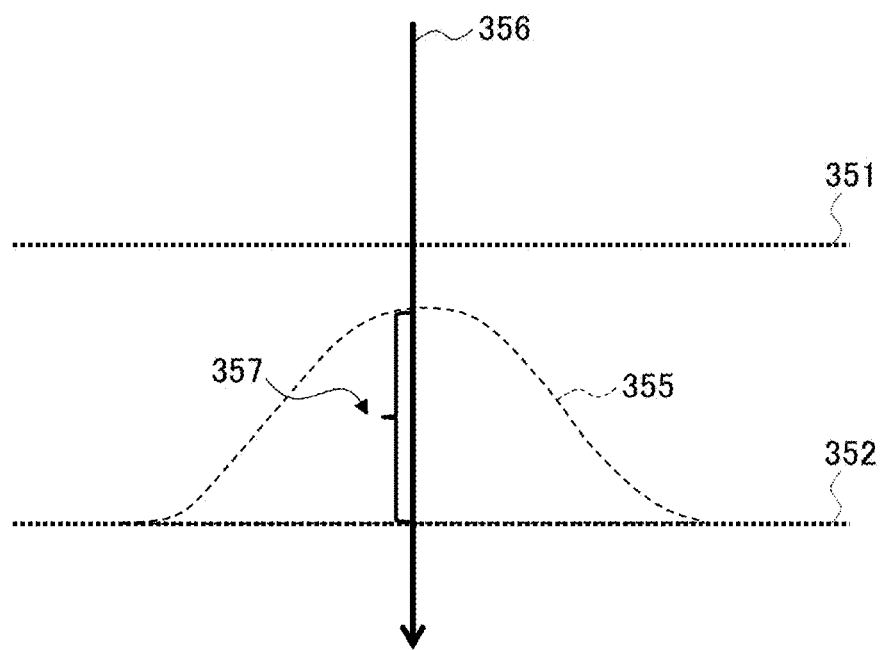
FIG. 6E is a schematic diagram for describing a usage mode of the photocoagulation apparatus according to the embodiment example.

In the present example, the area denoted by the reference character 357 in FIG. 6E has been changed. The change information of some examples includes a value indicating the length of the change area 357. Further, the change information acquiring processor 232 may execute estimation of the size of the change area 355 (e.g., the area and the volume of a certain cross section) from the length of the change area 357. The change information acquiring processor 232 of some examples may execute estimation of the degree of the tissue change in the retina Er by comparing the brightness of the first A-scan image and the brightness of the second A-scan image with each other.

(S10: Display Change Image on Retinal Image)

The display controller 213 displays a change image based on the change information generated in the step S9 on the display device 300 together with a retinal image. Typically, the display controller 213 prepares the first layer and the second layer that is overlaid on the first layer. In addition, the display controller 213 displays the retinal image on the first layer and the change image on the second layer.

The retinal image may be, for example, any image depicting at least the surface of the retina Er. Further, the change information may include, for example, any of the position of the tissue change, the distribution of the tissue changes, the size of the tissue change, and the degree of the tissue change, as described above. The position of the tissue change is represented by, for example, a display position of the change image with respect to the retinal image. The distribution of the tissue changes is represented by, for example, a distribution (map) of a plurality of change images in the retinal image. The size of the tissue change is represented by, for example, the size of the change image in the retinal image. The degree of the tissue change is represented by, for example, the display color of the change image.

Figure 7A:
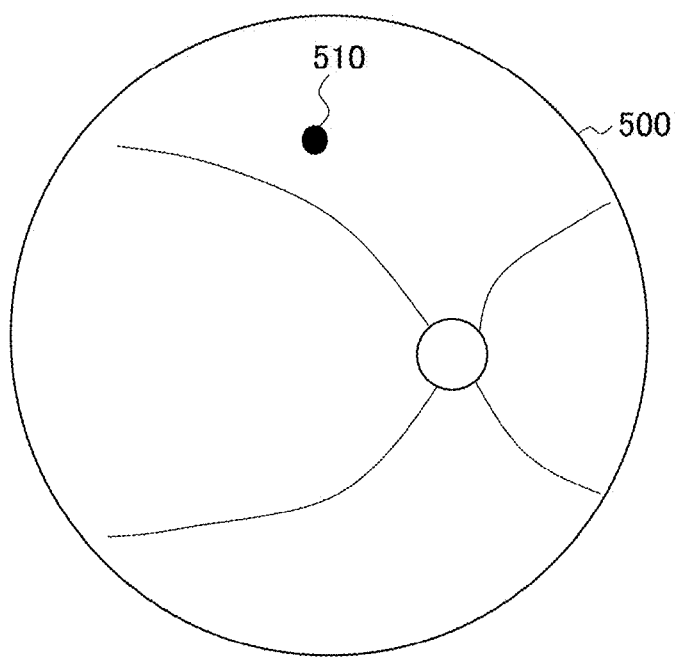
FIG. 7A is a schematic diagram for describing a usage mode of the photocoagulation apparatus according to the embodiment example.

FIG. 7A shows an example of the information displayed in the step S10. In the present example, the retinal image 500 is a front image of the retina Er of any type. The change image 510 may at least represent the position of the tissue change, and may further represent the size, degree, and the like of the tissue change. Note that the registration between the retinal image 500 and the change image 510 can be carried out, for example, by referring to a result of the registration between the retinal image 500 and an image acquired by the photography system 30 substantially at the same time as the application instruction of the treatment light being issued in the step S4. Similar processes of registration may also be employed in other steps.

Figure 7B:
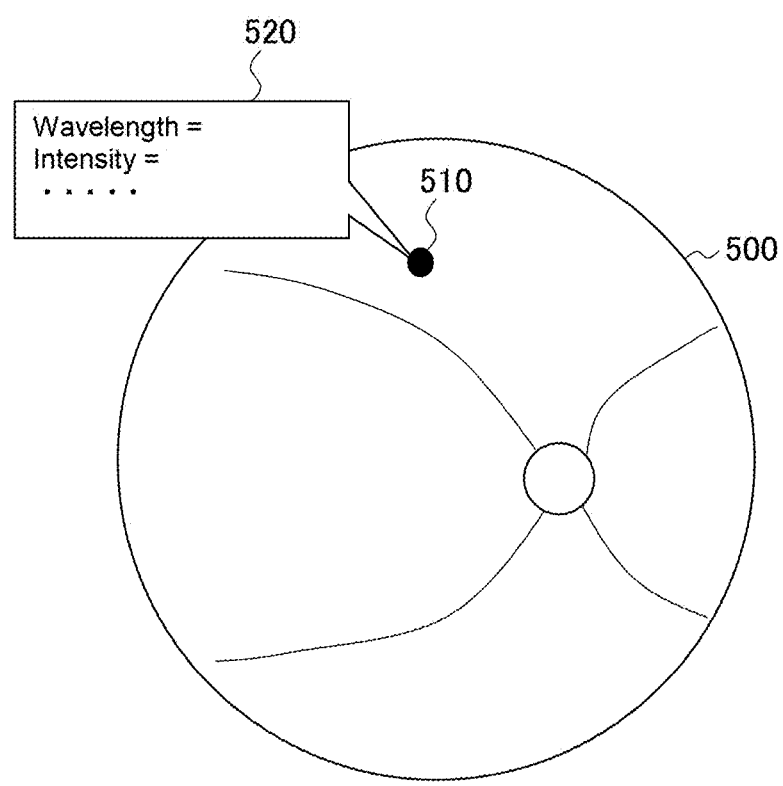
FIG. 7B is a schematic diagram for describing a usage mode of the photocoagulation apparatus according to the embodiment example.

The display controller 213 may read out the application condition applied in the step S6 (e.g., wavelength, intensity, application time, spot size, duty ratio, pulse width) from the memory 220, and then display the application condition together with the change image 510. For example, as shown in FIG. 7B, the application condition is presented in the balloon 520 that points to the change image 510. In some other examples, the application condition may be popped up in response to an operation of designating (e.g., clicking) the change image 510.

(S11: End Subthreshold Coagulation Treatment?)

The series of the steps S4 to S11 is repeated until the completion of the subthreshold coagulation treatment (S11:

No). Typically, each time the series of the steps S4 to S11 is repeated, the first A-scan is performed on a new location of the retina Er (S5), treatment light is applied to the new location (S6), the second A-scan is performed on the new location (S7), the first A-scan image and the second A-scan image corresponding to the new location are respectively constructed (S8), new change information is generated (S9), and a new change image is displayed in addition to previous change images (S10).

Figure 7C:
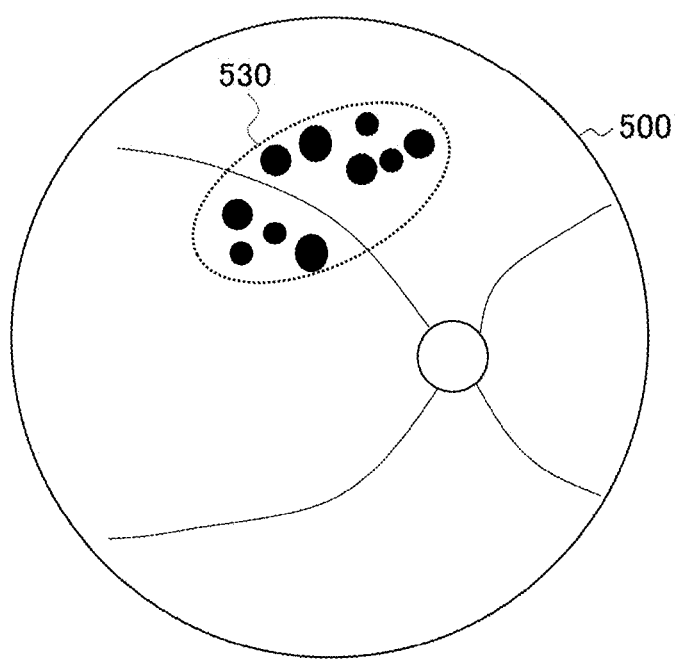
FIG. 7C is a schematic diagram for describing a usage mode of the photocoagulation apparatus according to the embodiment example.

FIG. 7C shows an example of the information displayed in the step S10 after the series of the steps S4 to S11 is repeated a plurality of times. In the present example, the change image group 530 corresponding to a plurality of treatment light applications is displayed on the retinal image 500. It should be noted that each change image represents a tissue change in a deep part of the retina, that is, each change image does not represent a coagulation spot on the retinal surface.

(S12: Acquire OCT Image of Entire Treatment Area)

After performing the applications of the treatment light to the plurality of positions on the retina Er, the scan controller 212 may control the OCT system 40 to apply an OCT scan to an area including all of the plurality of application positions. The OCT image constructing processor 231 constructs an OCT image from the data acquired by the OCT scan performed on the area.

Figure 8A:
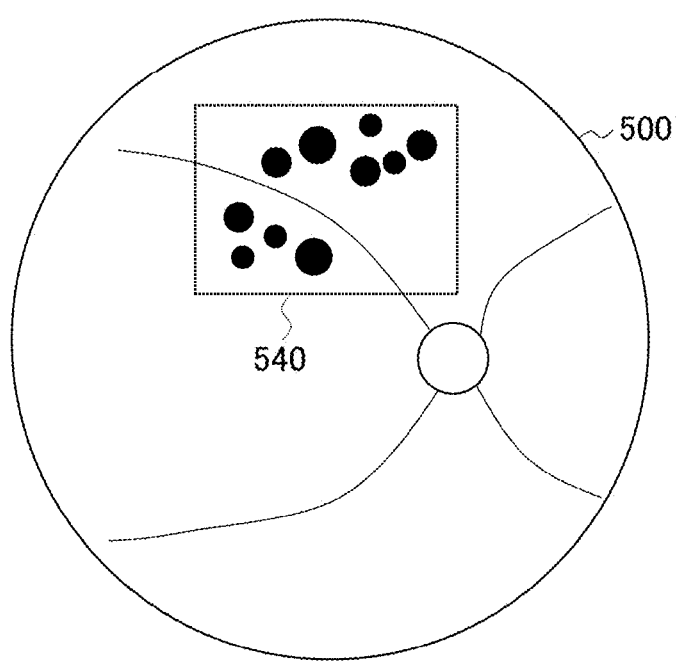
FIG. 8A is a schematic diagram for describing a usage mode of the photocoagulation apparatus according to the embodiment example.

FIG. 8A shows an example of the OCT scan area in the step S12. In the case where the plurality of change images shown in FIG. 7C (the change image group 530) is displayed, the scan controller 212 may control the OCT system 40 to apply an OCT scan to the area 540 that includes all of these change images.

Figure 8B:
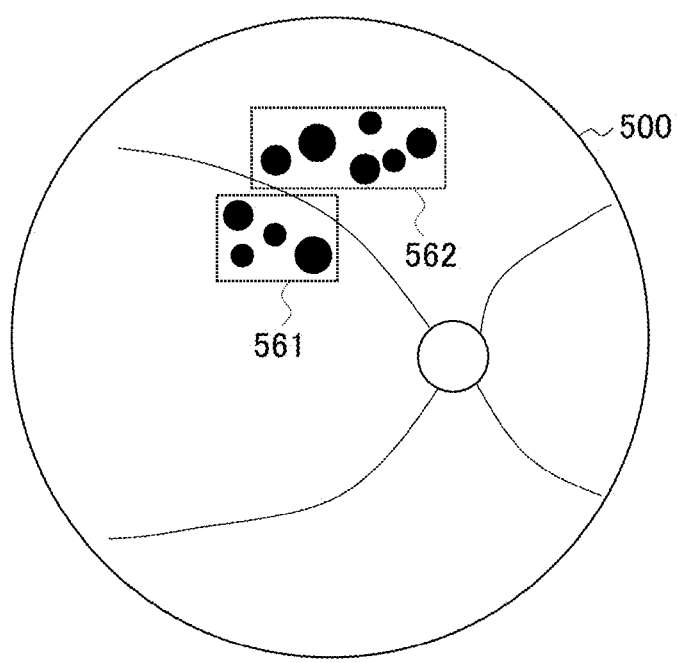
FIG. 8B is a schematic diagram for describing a usage mode of the photocoagulation apparatus according to the embodiment example.

While the single area 540 (connected region) that includes all of the change images is employed in the present example, two or more areas (two or more connected regions) that include all of the change images may be employed in some other examples. For example, in the case where the plurality of change images shown in FIG. 7C (the change image group 530) is displayed, the scan controller 212 may employ the two areas 561 and 562 shown in FIG. 8B.

(S13: Generate Change Distribution Information)

The change information acquiring processor 232 compares (the plurality of) the first A-scan image(s) constructed in the step S8 and the OCT image acquired in the step S12 with each other. From this comparison, the change information acquiring processor 232 generates the first change distribution information representing a distribution of the tissue changes in the retina Er over the scan area applied in the step S12. The first change distribution information represents the tissue changes in the period from a time point before the application of the treatment light up to a time point at which the OCT scan of the step S12 has been performed.

Further, the change information acquiring processor 232 may compare (the plurality of) the second A-scan image(s) constructed in the step S8 and the OCT image acquired in the step S12 with each other. Based on the comparison, the change information acquiring processor 232 may generate the second change distribution information representing a distribution of the tissue changes in the retina Er over the area that includes all of the treatment light application positions. The second change distribution information represents the tissue changes in the period from a time point immediately after the application of the treatment light up to a time point at which the OCT scan of the step S12 has been performed.

Each of the first change distribution information and the second change distribution information may represent any of the positional distribution of tissue changes caused by the treatment light, the sizes of the tissue changes, the degrees of the tissue changes, and the like.

(S14: Display Change Distribution Image on Retinal Image)

The display controller 213 displays the first change distribution image based on the first change distribution information generated in the step S13 on the display device 300 together with a retinal image. The retinal image may be the same image of the same type as the retinal image displayed in the step S10, may be a different image of the same type, or may be an image of a different type. The first change distribution image is a visualization of the tissue changes in the period from a time point before the application of the treatment light up to a time point at which the OCT scan of the step S12 has been performed.

In the case where the second change distribution information has been acquired in the step S13, the display controller 213 may display the second change distribution image based on the second change distribution information on the display device 300 together with a retinal image. The retinal image may be the same image of the same type as the retinal image displayed in the step S10, may be a different image of the same type, or may be an image of a different type. The second change distribution image is a visualization of the tissue changes in the period from a time point immediately after the application of the treatment light up to a time point at which the OCT scan of the step S12 has been performed.

(S15: Create Treatment Report)

The report creating processor 233 reads out a template of a treatment report from the memory 220 and enters data into the template based at least on the information acquired by the change information acquiring processor 232.

In the present example, the report creating processor 233 may enter any of the following types of information into the template, and may enter data obtained from any of the following types of information into the template: (1) the moving image or a frame therein obtained by the moving image photography started in the step S2: (2) the first A-scan image constructed in the step S8: (3) the second A-scan image constructed in the step S8: (4) the change information generated in the step S9: (5) the change image and/or the retinal image displayed in the step S10: (6) the OCT image acquired in the step S12: (7) the change distribution information generated in the step S13; and (8) the change distribution image and/or the retinal image displayed in the step S14.

The report creating processor 233 may also enter, into the template, data from the electronic medical record of the patient, an image of the patient's eye E acquired by another apparatus, or the like.

The treatment report created in the step S15 is typically sent to a database such as an electronic medical record system and saved on the database. This terminates the usage mode of the present example (End).

<Second Usage Mode>

Figure 9A:
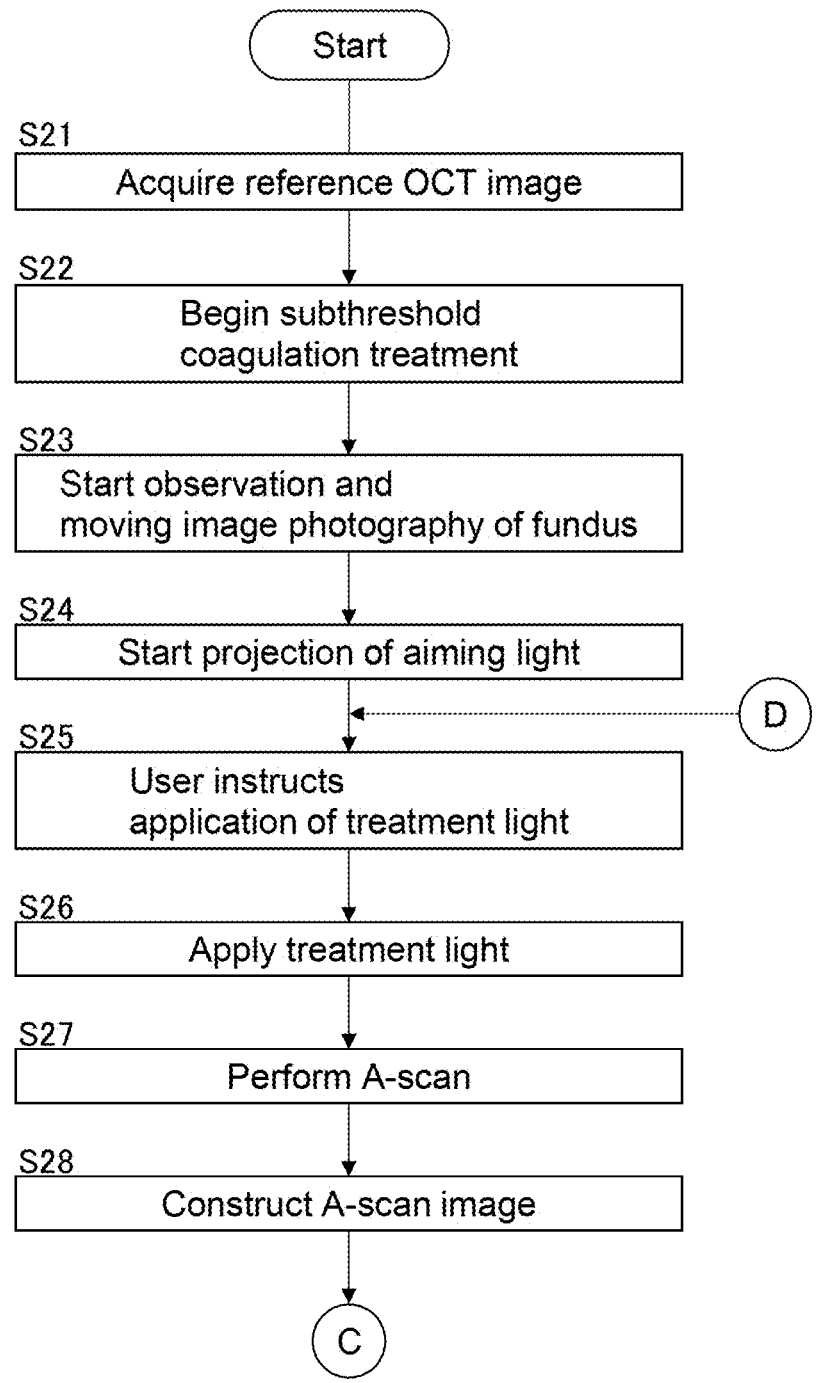
FIG. 9A is a flowchart illustrating a usage mode of the photocoagulation apparatus according to the embodiment example.
Figure 9B:
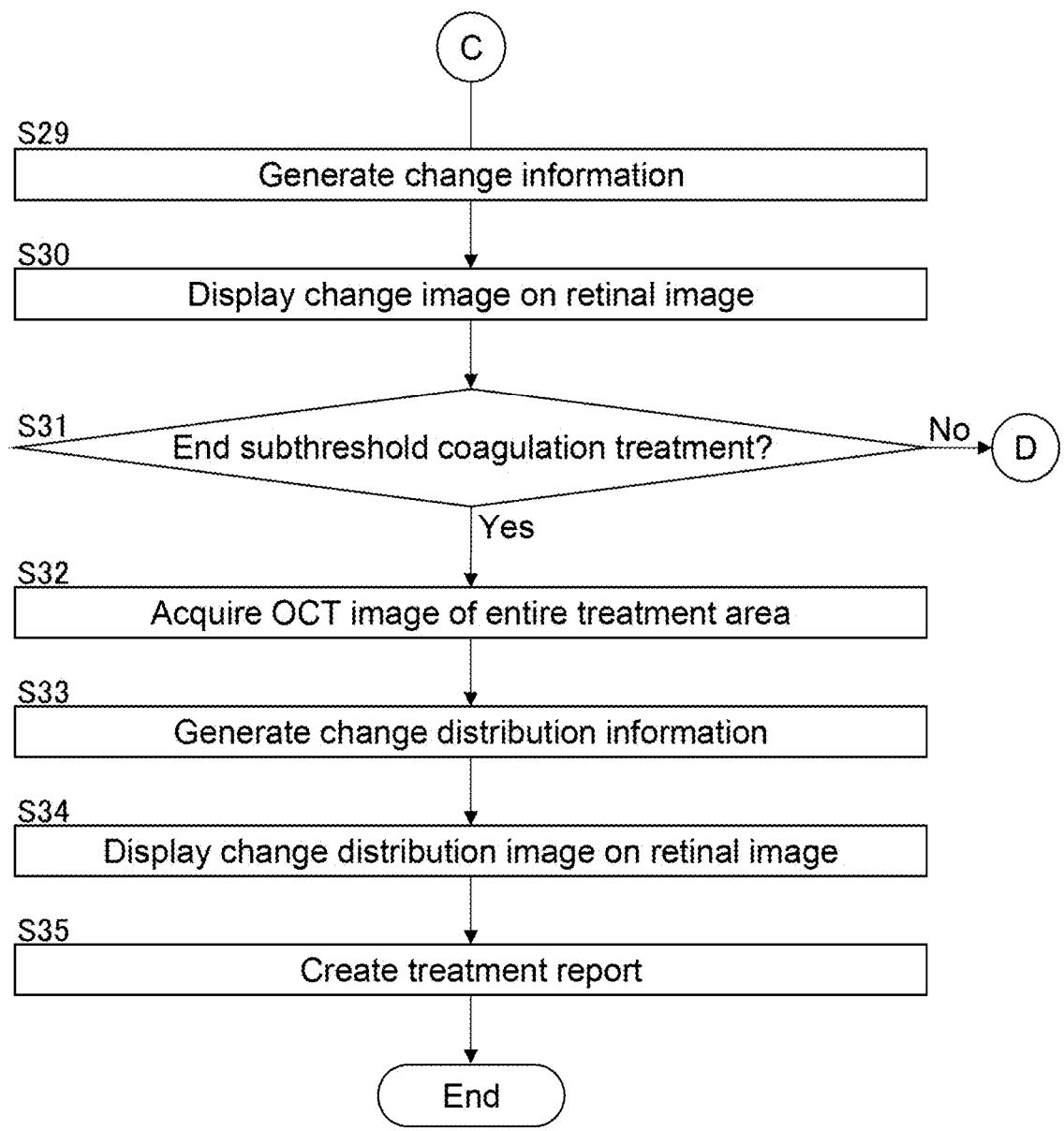
FIG. 9B is a flowchart illustrating a usage mode of the photocoagulation apparatus according to the embodiment example.

FIG. 9A and FIG. 9B show the flow of another usage mode example. The present example is operated to first acquire a reference OCT image and perform an OCT scan after the application of treatment light.

(S21: Acquire Reference OCT Image)

Prior to the commencement of photocoagulation treatment (subthreshold coagulation treatment), the photocoagulation apparatus 1 acquires a reference OCT image of the fundus Ef of the patient's eye E (the retina Er). The reference OCT image is a wide area OCT image of the retina Er. The reference OCT image is stored in the memory 220.

OCT scanning for constructing the reference OCT image is performed by the photocoagulation apparatus 1 or another OCT apparatus. In the case where the photocoagulation apparatus 1 performs the OCT scanning, the photocoagulation apparatus 1 (the OCT image constructing processor 231) may also carry out the construction of the reference OCT image. In the case where another OCT apparatus performs the OCT scanning, the photocoagulation apparatus 1 or an apparatus other than the photocoagulation apparatus 1 carries out the construction of the reference OCT image.

In addition, as with the first usage mode, the photocoagulation apparatus 1 may perform acquisition of a retinal image prior to the commencement of subthreshold coagulation treatment. Note that the photocoagulation apparatus 1 may acquire a retinal image at an arbitrary time point after the commencement of subthreshold coagulation treatment. The retinal image thus acquired is stored in the memory 220.

(S22: Begin Subthreshold Coagulation Treatment)

The user (doctor) conducts predetermined preparatory operations such as activation of the photocoagulation apparatus 1 and insertion of the probe 4 into the patient's eye E. Then, the user starts subthreshold coagulation treatment.

(S23: Start Observation and Moving Image Photography of Fundus)

Observation of the fundus Ef and moving image photography of the fundus Ef may be started in the same manner as that of the step S2 of the first usage mode.

(S24: Start Projection of Aiming Light)

Projection of the aiming light is started in the same manner as that of the step S3 of the first usage mode.

(S25: User Instructs Application of Treatment Light)

The user issues an instruction to start application of treatment light in the same manner as that of the step S4 of the first usage mode.

(S26: Apply Treatment Light)

The laser controller 211 receives the instruction for treatment light application and then controls the laser unit 7 to output treatment light. The treatment light output is applied to the retina Er via the optical fiber 3 and the probe 4. The photocoagulation apparatus 1 may record an application condition(s) of the treatment light in the memory 220.

(S27: Perform A-Scan)

The scan controller 212 controls the OCT unit 8 to perform an OCT scan on the retina Er again immediately after the application of the treatment light in the step S26 is executed. The OCT scan is performed in the same manner as the second A-scan in the step S7 of the first usage mode.

(S28: Construct A-Scan Image)

The OCT image constructing processor 231 constructs an A-scan image from data acquired by the A-scan performed in the step S27.

(S29: Generate Change Information)

The change information acquiring processor 232 generates change information representing a tissue change in the retina Er caused by the treatment light applied in the step S26, by comparing the reference OCT image acquired in the step S21 and the A-scan image constructed in the step S28 with each other. Registration between the reference OCT image and the A-scan image is performed in the same manner as in the first usage mode.

(S30: Display Change Image on Retinal Image)

The display controller 213 displays a change image based on the change information generated in the step S29 on the display device 300 together with a retinal image. The display control is executed in the same manner as in the step S10 of the first usage mode.

(S31: End Subthreshold Coagulation Treatment?)

The series of the steps S25 to S31 is repeated until the completion of the subthreshold coagulation treatment (S31: No). Typically, each time the series of the steps S25 to S31 is repeated, treatment light is applied to a new location of the retina Er (S26), an A-scan is performed on the new location (S27), an A-scan image corresponding to the new location is constructed (S28), new change information is generated (S29), and a new change image is displayed in addition to previous change images (S30).

(S32: Acquire OCT Image of Entire Treatment Area)

An OCT image of the entire area to which the subthreshold coagulation has been applied is acquired in the same manner as in the step S12 of the first usage mode.

(S33: Generate Change Distribution Information)

The change information acquiring processor 232 compares the reference OCT image acquired in the step S21 and the OCT image acquired in the step S32 with each other. Based on the comparison, the change information acquiring processor 232 generates the first change distribution information representing a distribution of the tissue changes in the retina Er over the scan area applied in the step S32. The first change distribution information represents the tissue changes in the period from a time point before the application of the treatment light up to a time point at which the OCT scan of the step S32 has been performed.

Further, the change information acquiring processor 232 may compare (the plurality of) the A-scan image(s) constructed in the step S28 and the OCT image acquired in the step S32 with each other. Based on the comparison, the change information acquiring processor 232 may generate the second change distribution information representing a distribution of the tissue changes in the retina Er over the area that includes all of the treatment light application positions. The second change distribution information represents the tissue changes in the period from a time point immediately after the application of the treatment light up to a time point at which the OCT scan of the step S32 has been performed.

Each of the first change distribution information and the second change distribution information may represent any of the positional distribution of tissue changes caused by the treatment light, the sizes of the tissue changes, the degrees of the tissue changes, and the like.

(S34: Display Change Distribution Image on Retinal Image)

The first change distribution image is displayed together with a retinal image in the same manner as in the step S14 of the first usage mode. The first change distribution image is a visualization of the tissue changes in the period from a time point before the application of the treatment light up to a time point at which the OCT scan of the step S32 has been performed.

Furthermore, the second change distribution image is displayed together with a retinal image in the same manner as in the step S14 of the first usage mode. The second change distribution image is a visualization of the tissue changes in the period from a time point immediately after the application of the treatment light up to a time point at which the OCT scan of the step S32 has been performed.

(S35: Create Treatment Report)

A treatment report is created in the same manner as in the step S15 of the first usage mode. The treatment report created is typically sent to a database such as an electronic medical record system and saved on the database. This terminates the usage mode of the present example (end).

<Effects>

Some effects of the photocoagulation apparatus 1 will be described.

The photocoagulation apparatus 1 is used to apply subthreshold coagulation to the retina Er via the probe 4 inserted in the eye. The photocoagulation apparatus 1 includes: the laser unit 7, the optical fiber 3, and the probe 4 (the laser projecting system); the OCT unit 8, the optical fiber 3, and the probe 4 (the first OCT system); the controller 210; the memory 220 (the first memory); the OCT image constructing processor 231 (the image constructing processor); the change information acquiring processor 232; and the display controller 213.

The laser projecting system is configured to apply the treatment light for subthreshold coagulation to the retina Er via the probe 4.

The first OCT system is configured to apply an OCT scan to the retina Er via the probe 4.

The controller 210 is configured to perform, upon receiving an instruction from the user, both control of the laser projecting system to apply the treatment light to the retina Er and control of the first OCT system to apply an OCT scan to the retina Er at least after the application of the treatment light. In the present embodiment example, the former control is executed by the laser controller 211, and the latter control is executed by the scan controller 212.

The memory 220 is configured to store the first OCT image constructed from data acquired by an OCT scan applied to the retina Er before the application of the treatment light.

The OCT image constructing processor 231 is configured to construct the second OCT image from data acquired by an OCT scan applied to the retina Er after the application of the treatment light.

The change information acquiring processor 232 is configured to acquire change information representing a tissue change in the retina Er caused by the treatment light, by comparing the first OCT image and the second OCT image with each other.

The display controller 213 is configured to display a change image based on the change information on the display device 300 together with a retinal image.

The display device 300 may be in any form. For example, the display device 300 may be a general display, a display mounted on the photocoagulation apparatus 1, a head-up display used for stereoscopic observation of the retina Er, or a display mounted on polarized glasses worn for stereoscopic viewing with the head-up display.

According to the photocoagulation apparatus 1 as described above, the state of tissue changes caused by the treatment light can be acquired and visualized in real time, based on the first OCT image representing the state of a retinal tissue before the application of the treatment light for subthreshold coagulation and also on the second OCT image representing the state of the retinal tissue after the application of the treatment light. In other words, the photocoagulation apparatus 1 is capable of visualizing in real time and appropriately presenting to the user, the state of tissue changes in a deep part of the retina that occur in the subthreshold coagulation treatment. With this, the subthreshold coagulation treatment, which is conducted using a probe inserted in the eye, can be properly carried out.

In the present embodiment example, an OCT scan may be conducted both before and after the application of the treatment light. To be more specific, the controller 210 may be configured to perform the first control of the first OCT system to apply an OCT scan to the retina Er for acquiring the first OCT image, perform control of the laser projecting system for applying the treatment light to the retina Er after the first control, and perform the second control of the first OCT system to apply an OCT scan for acquiring the second OCT image after the control of the laser projecting system.

Such a configuration example provides a specific configuration for acquiring both the first OCT image and the second OCT image. In addition to this, the configuration of this example has an advantage that the registration between the first OCT image and the second OCT image is not required.

Each of the OCT scan applied by the first control and the OCT scan applied by the second control may be an A-scan in the present configuration example.

According to such a configuration example, respective OCT scans before and after the application of the treatment light can be performed in a short period of time. Therefore, deviation between the scan positions of the both OCT scans is reduced. Also, a series of operations, which consists of OCT scanning, treatment light application, and another OCT scanning, can be conducted in a short period of time. The configuration, thus, does not interfere with the processes of applying subthreshold coagulation to a plurality of locations in the retina one after another.

In instead of performing an OCT scan before each treatment light application, the present embodiment example may acquire the first OCT image in advance. More specifically, the first OCT image may be a three dimensional OCT image constructed from data acquired by applying an OCT scan to a three dimensional region of the retina Er (referred to as the reference OCT image).

Such a configuration example provides a specific configuration for obtaining both the first OCT image and the second OCT image. Furthermore, according to the present configuration example, no OCT scanning is required before each treatment light application. Consequently, the present configuration example has an advantage that the respective operations corresponding to each treatment light application can be performed in a short period of time, thereby not interfering with the task of applying subthreshold coagulation to a plurality of locations of the retina one after another.

In the present configuration example, the OCT scan applied to the retina Er after the application of the treatment light may be an A-scan.

According to such a configuration example, the time required to perform the respective operations corresponding to each treatment light application can further be shortened.

The controller 210 of the present embodiment example may be configured to perform the control of the first OCT system to apply an OCT scan to the retina Er each time the control of the laser projecting system to apply the treatment light to the retina Er is performed. In the case where such a configuration example is employed, the OCT image constructing processor 231 may construct the second OCT image each time the first OCT system performs the OCT scan. Further, the change information acquiring processor 232 may acquire the change information each time the OCT image constructing processor 231 executes construction of the second OCT image. In addition, the display controller 213 may update a display of a change image provided to the user together with the retinal image each time the change information acquiring processor 232 executes acquisition of the change information.

Such a configuration example makes it possible to update the display of a change image representing a tissue change in a deep part of the retina each time treatment light is applied to the retina Er. For example, a change image representing a tissue change in a deep part of the retina caused by another treatment light can be added each time treatment light is newly applied to the retina Er. Therefore, the photocoagulation apparatus 1 can visualize in real time and appropriately present to the user, the state of tissue changes in a deep part of the retina that occur in the subthreshold coagulation treatment.

In the present embodiment example, the controller 210 may be configured to perform the control of the first OCT system to apply the OCT scan to the retina Er immediately after the control of the laser projecting system to apply the treatment light to the retina Er. Such a configuration example makes it possible to achieve both applications of the treatment light at short time intervals and real time visualization of the state of tissue changes in a deep part of the retina.

The photocoagulation apparatus 1 of the present embodiment example may further include the OCT system 40 (the second OCT system) configured to apply an OCT scan, after the treatment light is applied to each of a plurality of positions on the retina Er, to an area that includes all of the plurality of positions. The OCT image constructing processor 231 may construct the third OCT image from data acquired by the OCT system 40. Further, the change information acquiring processor 232 may acquire the first change distribution information representing a distribution of tissue changes in the retina Er in the area by comparing the first OCT image and the third OCT image with each other. Moreover, the display controller 213 may control the display device 300 to display the first change distribution image based on the first change distribution information together with a retinal image.

According to such a configuration example, the photocoagulation apparatus 1 becomes capable of acquiring an OCT image of the entire treatment area after subthreshold coagulation treatment is performed on a plurality of positions on the retina Er, and then visualizing the distribution and/or state of tissue changes. Here, the first change distribution information represents tissue changes in a deep part of the retina between before and after the subthreshold coagulation treatment.

The change information acquiring processor 232 of the present embodiment example may be configured to acquire the second change distribution information representing a distribution of tissue changes in the retina Er over the area that includes all of the plurality of positions on the retina Er, to each of which the subthreshold coagulation is applied, by comparing the second OCT image and the third OCT image with each other. The display controller 213 may control the display device 300 to display the second change distribution image based on the second change distribution information together with a retinal image.

According to such a configuration example, the photocoagulation apparatus 1 becomes capable of acquiring an OCT image of the entire treatment area after subthreshold coagulation treatment is performed on a plurality of positions on the retina Er, and then visualizing the distribution and state of tissue changes. Here, the second change distribution information represents tissue changes in a deep part of the retina between immediately after application of the treatment light to each of the plurality of positions on the retina Er and after the subthreshold coagulation treatment.

The change information acquiring processor 232 of the present embodiment example may be configured to construct motion contrast data from two or more OCT images acquired from substantially the same position (substantially the same location) of the retina Er at different times, and determine a tissue change in the retina Er from the motion contrast data.

Such a configuration example makes it possible to acquire any of the change information, the first change distribution information, and the second change distribution information, by using a motion contrast technique like OCT angiography.

The display controller 213 of the present embodiment example may be configured to display the retinal image on the first layer, and displays, on the second layer overlaid on the first layer, an image based on information acquired by the change information acquiring processor 232.

Such a configuration example makes it possible to provide a specific method or technique for displaying any one or more of the change image, the first change distribution image, and the second change distribution image on the retinal image. In addition, such a configuration makes it possible to facilitate the update of the change image and the like.

The display controller 213 of the present embodiment example may be configured to display the application condition of the treatment light applied to the retina Er by the laser projecting system together with the image based on the information acquired by the change information acquiring processor 232.

According to such a configuration example, the photocoagulation apparatus 1 becomes capable of providing to the user the application condition (e.g., wavelength, intensity, application time, spot size, duty ratio, pulse width) of the treatment light applied to the retina Er together with any of the change image, the first change distribution image, and the second change distribution image.

The photocoagulation apparatus 1 of the present embodiment example may further include the memory 220 (the second memory) and the report creating processor 233. The memory 220 is configured to store a template of a treatment report in advance. The report creating processor 233 may enter data in the template based at least on the information acquired by the change information acquiring processor 232.

Such a configuration example allows the photocoagulation apparatus 1 to automatically create a treatment report on the basis of any of the change information, the first change distribution information, the second change distribution information, the change image, the first change distribution image, and the second change distribution image, and/or, on the basis of data based on any of them.

The retinal image of the present embodiment example may be any of an image of the retina Er acquired by a fundus camera, an image of the retina Er acquired by a scanning laser ophthalmoscope, an image of the retina Er acquired by a surgical microscope, an image of the retina Er acquired by a slit lamp microscope, and a front image of the retina Er acquired by using OCT.

According to such a configuration, the photocoagulation apparatus 1 can display any of the change image, the first change distribution image, and the second change distribution image together with a retinal image of a desired type.

Modification Examples

A photocoagulation apparatus of some modification examples is configured to be capable of presenting various kinds of information within the observation field of view of a stereoscopic image obtained by a microscope. For example, the photocoagulation apparatus of some modification examples may be capable of presenting, within the observation field of view of a stereoscopic image obtained by a microscope, any of a retinal image, a change image, the first change distribution image, the second change distribution image, the application condition of the treatment light, and the like.

Figure 10:
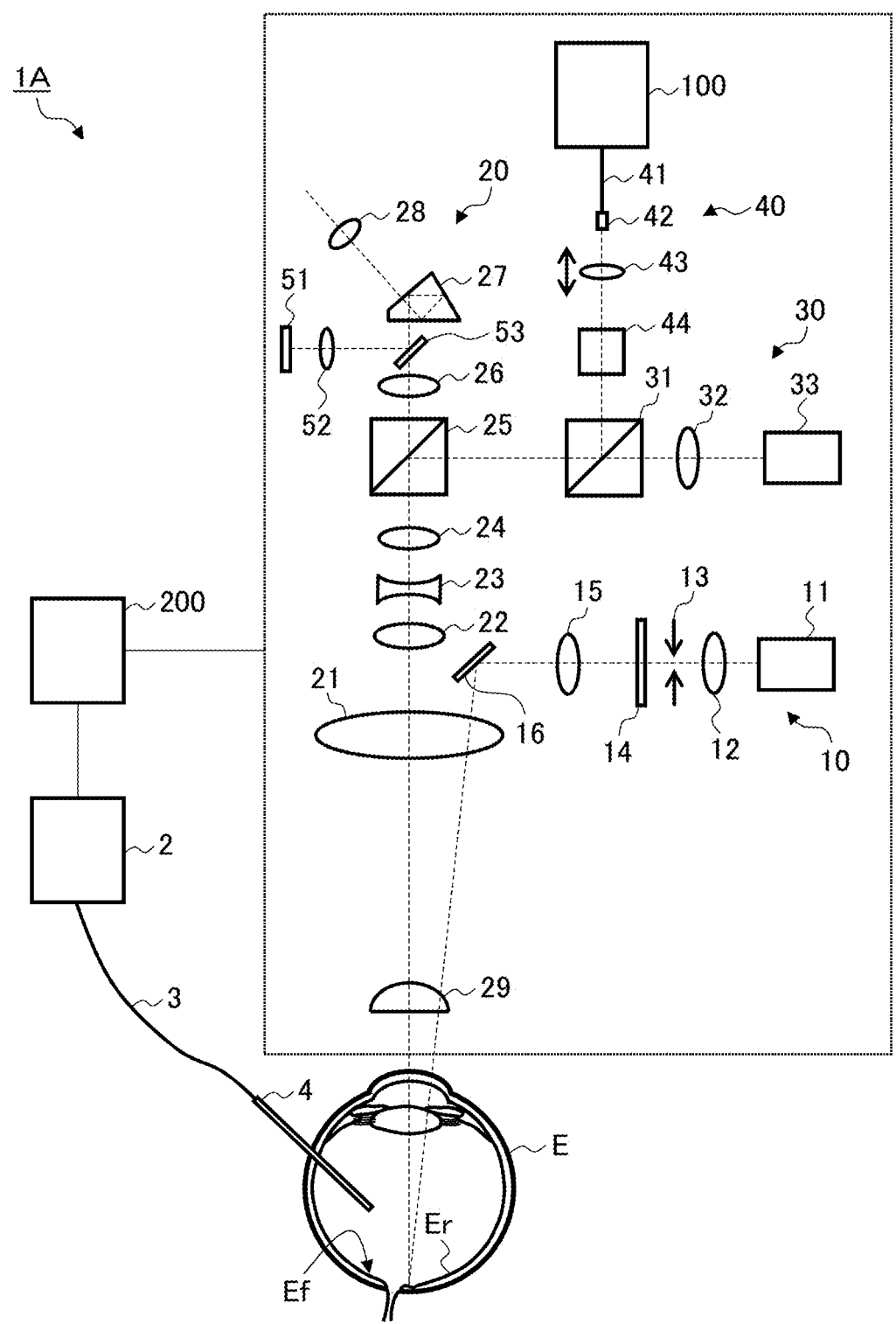
FIG. 10 is a schematic diagram illustrating the configuration of the photocoagulation apparatus according to the modification example.

FIG. 10 shows an example of a configuration that may be employed to realize such a function. The same or similar elements as or to those of the photocoagulation apparatus 1 according to the above embodiment example are denoted by the same reference characters, and the descriptions thereof will be omitted unless otherwise mentioned.

The photocoagulation apparatus 1A shown in FIG. 10 is different from the photocoagulation apparatus 1 according to the above embodiment example in that the photocoagulation apparatus 1A additionally includes the display device 51, the imaging lens 52, and the beam splitter 53, and does not include the display device 300 of the photocoagulation apparatus 1. The elements apart from those listed above may respectively be the same as or similar to the corresponding elements of the photocoagulation apparatus 1 of the embodiment example described above (see FIG. 2 to FIG. 4).

The photocoagulation apparatus 1A is used to apply subthreshold coagulation to the retina Er via the probe 4 inserted into the eye. The photocoagulation apparatus 1A includes: the laser unit 7, the optical fiber 3, and the probe 4 (the laser projecting system): the OCT unit 8, the optical fiber 3, and the probe 4 (the first OCT system): the controller 210: the memory 220 (the first memory): the OCT image constructing processor 231 (the image constructing processor): the change information acquiring processor 232; and the display controller 213. These elements may respectively be the same as those of the photocoagulation apparatus 1 according to the embodiment example described above.

In addition to them, the photocoagulation apparatus 1A includes the display device 51 in place of the display device 300, and also includes the imaging lens 52 and the beam splitter 53. Further, the photocoagulation apparatus 1A explicitly uses the observation system 20.

The observation system 20 includes an optical system configured for the user to observe a magnified image of the retina Er via the eyepiece 28.

The imaging lens 52 and the beam splitter 53 are disposed in an optical path starting from the display device 51.

The beam splitter 31 (an optical path coupling member) is, for example, a half mirror, and is configured and arranged to couple the optical path starting from the display device 51 with the optical path of the observation system 20 that continues up to the eyepiece 28.

In the present modification example, an OCT scan may be conducted both before and after the application of the treatment light. To be more specific, the controller 210 may be configured to perform the first control of the first OCT system to apply an OCT scan to the retina Er to acquire the first OCT image, perform the control of the laser projecting system to apply the treatment light to the retina Er after the first control, and perform the second control of the first OCT system to apply an OCT scan to acquire the second OCT image after the control of the laser projecting system.

In the present configuration example, the OCT scan applied by the first control and the OCT scan applied by the second control each may be an A-scan.

The present modification example may acquire the first OCT image in advance, instead of performing an OCT scan before each treatment light application. More specifically, the first OCT image may be the reference OCT image that is a three dimensional OCT image constructed from data acquired by applying an OCT scan to a three dimensional region of the retina Er.

In the present configuration example, the OCT scan applied to the retina Er after the application of the treatment light may be an A-scan.

The display controller 213 may be configured to display a change image based on the change information acquired by the change information acquiring processor 232 on the display device 51 together with a retinal image. Further, the display controller 213 may be configured to update a display of the change image presented to the user together with the retinal image each time the change information is acquired by the change information acquiring processor 232.

The display controller 213 may be configured to control the display device 51 to display the first change distribution image based on the first change distribution information acquired by the change information acquiring processor 232 together with a retinal image. Further, the display controller 213 may be configured to control the display device 51 to display the second change distribution image based on the second change distribution information acquired by the change information acquiring processor 232 together with a retinal image.

The display controller 213 may be configured to display the retinal image on the first layer, and displays, on the second layer overlaid on the first layer, an image based on information acquired by the change information acquiring processor 232. The information acquired by the change information acquiring processor 232 may be any of the change image, the first change distribution image, and the second change distribution image, for example.

The display controller 213 may be configured to display the application condition (e.g., wavelength, intensity, application time, spot size, duty ratio, pulse width) of the treatment light applied to the retina Er by the laser projecting system together with an image generated based on the information acquired by the change information acquiring processor 232 (e.g., the change image, the first change distribution image, the second change distribution image).

In addition to some effects of the photocoagulation apparatus 1 of the above embodiment example, the configuration of the present modification example is capable of presenting various kinds of information within the observation field of view of the stereoscopic image provided to the user through the observation system 20.

Any of the configurations (elements) and/or any of the functions of the photocoagulation apparatus 1 according to the above embodiment example may be combined with the photocoagulation apparatus 1A according to the present modification example. Further, any known method or technique may be combined with the photocoagulation apparatus 1A according to the present modification example.

<Control Method, Program, Recording Medium>

A description will be given of a control method, a program, and a recording medium according to some embodiment examples.

A control method corresponding to the above photocoagulation apparatus 1 (or 1A) will be described. The control method is a method of controlling a photocoagulation apparatus (1). The photocoagulation apparatus (1) includes a laser projecting system and an optical coherence tomography (OCT) system (the OCT unit 8). The laser projecting system is configured to apply treatment light for subthreshold coagulation to a retina (Er) via a probe (4) inserted in an eye and the OCT system is configured to apply an OCT scan to the retina (Er) via the probe (4).

The control method of the photocoagulation apparatus (1) includes a control step, a memory step, an image constructing step, a change information acquiring step, and a display control step.

The control step performs, upon receiving an instruction from a user, control of the laser projecting system to apply the treatment light to the retina (Er) and control of the OCT system to apply an OCT scan to the retina (Er) at least after the application of the treatment light:

The memory step stores the first OCT image constructed from data acquired by an OCT scan applied to the retina (Er) before the application of the treatment light.

The image constructing step constructs the second OCT image from data acquired by the OCT scan applied to the retina (Er) after the application of the treatment light.

The change information acquiring step acquires change information representing a tissue change in the retina (Er) caused by the treatment light by comparing the first OCT image and the second OCT image with each other.

The display control step displays a change image based on the change information on a display device (300, 51) together with a retinal image.

According to the control method of the photocoagulation apparatus (1) as described above, the state of tissue changes caused by the treatment light can be acquired and visualized in real time based on the first OCT image representing the state of a retinal tissue before the application of the treatment light for subthreshold coagulation and the second OCT image representing the state of a retinal tissue after the application of the treatment light. In other words, the control method makes it possible to visualize in real time and appropriately present to the user, the state of tissue changes in a deep part of the retina that occur in the subthreshold coagulation treatment. With this, the subthreshold coagulation treatment performed by inserting a probe into the eye can be properly carried out.

Any of the functions, any of the processing, any of the processes, any of the operations, etc. described in any of the above-described embodiment examples can be combined with the control method according to the present embodiment example.

It is possible to configure a program that causes a computer (200) to execute the control method of the photocoagulation apparatus (1) according to the present embodiment example. In addition, it is possible to create a computer-readable non-transitory recording medium that stores the program configured in this way. The non-transitory recording medium may be in any form, and examples thereof include a magnetic disk, an optical disk, a magneto-optical disk, a semiconductor memory, and the like.

The embodiment examples described above are merely typical examples of the present disclosure. Therefore, any modification (omission, substitution, replacement, addition, etc.) within the scope of the gist of the present disclosure may be appropriately applied.

What is claimed is:

1. A photocoagulation apparatus for applying subthreshold coagulation to a retina via a probe inserted in an eye, comprising:
   a laser projecting system configured to apply treatment light for subthreshold coagulation to the retina via the probe;
   a first optical coherence tomography (OCT) system configured to apply an OCT scan to the retina via the probe;
   a controller configured to perform, upon receiving an instruction from a user, control of the laser projecting system to apply the treatment light to the retina and control of the first OCT system to apply an OCT scan to the retina at least after application of the treatment light;
a first memory that stores a first OCT image constructed from data acquired by an OCT scan applied to the retina prior to the application of the treatment light;
an image constructing processor configured to construct a second OCT image from data acquired by the OCT scan applied to the retina after the application of the treatment light;
a change information acquiring processor configured to acquire change information representing a tissue change in the retina caused by the treatment light by comparing the first OCT image and the second OCT image with each other; and
a display controller configured to display a change image based on the change information on a display device together with a retinal image; and
a second OCT system configured to apply an OCT scan, after the treatment light is applied to each of a plurality of positions on the retina, to an area that includes all of the plurality of positions, wherein
the image constructing processor constructs a third OCT image from data acquired by the second OCT system,
the change information acquiring processor acquires first change distribution information representing a distribution of tissue changes in the retina in the area by comparing the first OCT image and the third OCT image with each other,
the display controller controls the display device to display a first change distribution image based on the first change distribution information together with a retinal image,
the change information acquiring processor acquires second change distribution information representing a distribution of tissue changes in the retina in the area that includes all of the plurality of positions by comparing the second OCT image and the third OCT image with each other, and
the display controller controls the display device to display a second change distribution image based on the second change distribution information together with a retinal image.

2. The photocoagulation apparatus of claim 1, wherein the controller performs first control of the first OCT system to apply an OCT scan to the retina to acquire the first OCT image, performs control of the laser projecting system to apply the treatment light to the retina after the first control, and performs second control of the first OCT system to apply an OCT scan to acquire the second OCT image after the control of the laser projecting system.

3. The photocoagulation apparatus of claim 2, wherein each of the OCT scan applied by the first control and the OCT scan applied by the second control is an A-scan.

4. The photocoagulation apparatus of claim 1, wherein the first OCT image is a three dimensional OCT image constructed from data acquired by applying an OCT scan to a three dimensional region of the retina.

5. The photocoagulation apparatus of claim 4, wherein the OCT scan applied to the retina after the application of the treatment light is an A-scan.

6. The photocoagulation apparatus of claim 1, wherein the controller performs the control of the first OCT system to apply the OCT scan to the retina each time the control of the laser projecting system to apply the treatment light to the retina is performed, the image constructing processor constructs the second OCT image each time the OCT scan is applied by the first OCT system,
the change information acquiring processor acquires the change information each time the second OCT image is constructed by the image constructing processor, and
the display controller updates a display of a change image provided to the user together with the retinal image each time the change information is acquired by the change information acquiring processor.

7. The photocoagulation apparatus of claim 6, wherein the controller performs the control of the first OCT system to apply the OCT scan to the retina immediately after the control of the laser projecting system to apply the treatment light to the retina.

8. The photocoagulation apparatus of claim 1, wherein the change information acquiring processor constructs motion contrast data from two or more OCT images acquired from substantially a same position of the retina at different times, and determines a tissue change in the retina from the motion contrast data.

9. The photocoagulation apparatus of claim 1, wherein the display controller displays the retinal image on a first layer, and displays, on a second layer overlaid on the first layer, an image based on information acquired by the change information acquiring processor.

10. The photocoagulation apparatus of claim 9, wherein the display controller displays an application condition of the treatment light applied to the retina by the laser projecting system together with the image based on the information acquired by the change information acquiring processor.

11. The photocoagulation apparatus of claim 1, further comprising:
a second memory that stores a template of a treatment report in advance; and
a report creating processor configured to enter data in the template based at least on information acquired by the change information acquiring processor.

12. The photocoagulation apparatus of claim 1, wherein the retinal image is any of an image of the retina acquired by a fundus camera, an image of the retina acquired by a scanning laser ophthalmoscope, an image of the retina acquired by a surgical microscope, an image of the retina acquired by a slit lamp microscope, and a front image of the retina acquired by using OCT.

13. The photocoagulation apparatus of claim 1, further comprising:
an observation system configured for the user to observe a magnified image of the retina via an eyepiece; and
an optical path coupling member configured to couple an optical path starting from the display device with an optical path of the observation system toward the eyepiece.

14. A method of controlling a photocoagulation apparatus that includes a laser projecting system configured to apply treatment light for subthreshold coagulation to a retina via a probe inserted in an eye and an optical coherence tomography (OCT) system configured to apply an OCT scan to the retina via the probe, the method comprising:
performing, upon receiving an instruction from a user, control of the laser projecting system to apply the treatment light to the retina and control of the OCT system to apply an OCT scan to the retina at least after the application of the treatment light;
storing a first OCT image constructed from data acquired by an OCT scan applied to the retina prior to the application of the treatment light;

constructing a second OCT image from data acquired by the OCT scan applied to the retina after application of the treatment light;

acquiring step of acquiring change information representing a tissue change in the retina caused by the treatment light by comparing the first OCT image and the second OCT image with each other;

displaying a change image based on the change information on a display device together with a retinal image;

applying an OCT scan, by a second OCT system, after the treatment light is applied to each of a plurality of positions on the retina, to an area that includes all of the plurality of positions;

constructing a third OCT image from data acquired by the second OCT system;

acquiring first change distribution information representing a distribution of tissue changes in the retina in the area by comparing the first OCT image and the third OCT image with each other;

displaying a first change distribution image based on the first change distribution information together with a retinal image;

acquiring second change distribution information representing a distribution of tissue changes in the retina in the area that includes all of the plurality of positions by comparing the second OCT image and the third OCT image with each other; and displaying a second change distribution image based on the second change distribution information together with a retinal image.

15. A computer-readable non-transitory recording medium storing a program causing a computer to execute the method of claim 14.

* * * * *